(12) United States Patent
Bryant et al.

(10) Patent No.: US 11,217,332 B1
(45) Date of Patent: Jan. 4, 2022

(54) DISTRIBUTED LEDGER SYSTEM FOR MANAGING MEDICAL RECORDS

(71) Applicant: STATE FARM MUTUAL AUTOMOBILE INSURANCE COMPANY, Bloomington, IL (US)

(72) Inventors: Ronny S. Bryant, Bloomington, IL (US); Stacie A. McCullough, Bloomington, IL (US); Mitchell J. Hill, Bloomington, IL (US); Jacob J. Alt, Downs, IL (US); Jaime Skaggs, Chenoa, IL (US); Shawn M. Call, Bloomington, IL (US); Eric Bellas, Bloomington, IL (US); Vicki King, Bloomington, IL (US); Melinda Teresa Magerkurth, Utica, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 382 days.

(21) Appl. No.: 15/870,298

(22) Filed: Jan. 12, 2018

Related U.S. Application Data

(60) Provisional application No. 62/548,668, filed on Aug. 22, 2017, provisional application No. 62/548,679, filed on Aug. 22, 2017, provisional application No. 62/548,682, filed on Aug. 22, 2017, provisional application No. 62/548,692, filed on Aug. 22, 2017, provisional application No. 62/548,741, filed on Aug. 22, 2017, provisional application No. 62/548,700, (Continued)

(51) Int. Cl.
*G06Q 40/00* (2012.01)
*G16H 10/60* (2018.01)
*G06Q 40/08* (2012.01)

(52) U.S. Cl.
CPC ............ *G16H 10/60* (2018.01); *G06Q 40/08* (2013.01)

(58) Field of Classification Search
CPC .............................. G06H 10/60; G06Q 40/08
USPC .................................................. 705/35–40, 4
See application file for complete search history.

(56) References Cited

U.S. PATENT DOCUMENTS 8,085,166 B2  12/2011  Tamir et al.
8,106,769 B1  1/2012   Maroney et al.
(Continued)

FOREIGN PATENT DOCUMENTS

WO  WO-2017145009 A1  8/2017
WO  WO-2021/046494 A1  3/2021

OTHER PUBLICATIONS

Mainelli etal: "Sharing ledgers for sharing economies: an exploration of mutual distributed ledgers (aka blockchain technology)", The Journal of Financial Perspectives: FinTech, EY Global Financial Services Institute, vol. 3—Issue 3, Winter 2015 (Year: 2015).*

(Continued)

*Primary Examiner* — Edward J Baird
(74) *Attorney, Agent, or Firm* — Marshall, Gerstein & Borun LLP

(57) ABSTRACT

Systems and methods are disclosed with respect to using a distributed ledger, such as a blockchain, for managing medical records. The medical records may be accessible by medical institutions such as hospitals, and may be controlled by the patient. The patient may, for example, decide which entities can access and/or edit the medical records.

16 Claims, 20 Drawing Sheets

Related U.S. Application Data filed on Aug. 22, 2017, provisional application No. 62/548,731, filed on Aug. 22, 2017, provisional application No. 62/548,748, filed on Aug. 22, 2017, provisional application No. 62/545,262, filed on Aug. 14, 2017, provisional application No. 62/508,133, filed on May 18, 2017, provisional application No. 62/500,049, filed on May 2, 2017, provisional application No. 62/500,326, filed on May 2, 2017.

(56) References Cited

U.S. PATENT DOCUMENTS

| | | |
|---|---|---|
| 8,374,957 B1 | 2/2013 | Garcia et al. |
| 8,756,085 B1 | 6/2014 | Plummer et al. |
| 9,141,582 B1 | 9/2015 | Brinkmann et al. |
| 9,998,286 B1 | 6/2018 | Ramathal et al. |
| 10,269,009 B1* | 4/2019 | Winklevoss ......... G06Q 20/105 |
| 10,341,309 B1 | 7/2019 | Ramirez et al. |
| 10,366,204 B2* | 7/2019 | Tanner, Jr. ............. G16H 40/20 |
| 10,430,889 B1 | 10/2019 | Ismaili et al. |
| 10,454,878 B2 | 10/2019 | Khan et al. |
| 10,510,120 B1 | 12/2019 | Roll |
| 10,521,780 B1 | 12/2019 | Hopkins, III et al. |
| 10,554,649 B1 | 2/2020 | Fields et al. |
| 10,586,062 B1 | 3/2020 | Rangan et al. |
| 10,606,669 B2 | 3/2020 | Jacobs et al. |
| 10,713,727 B1 | 7/2020 | Floyd et al. |
| 10,796,371 B1 | 10/2020 | Floyd et al. |
| 10,796,393 B2 | 10/2020 | Messerges et al. |
| 10,805,085 B1 | 10/2020 | Liang |
| 10,832,337 B1 | 11/2020 | Floyd et al. |
| 10,832,338 B1 | 11/2020 | Floyd et al. |
| 10,833,843 B1* | 11/2020 | Vijayvergia .............. H04L 9/30 |
| 10,872,381 B1 | 12/2020 | Leise et al. |
| 10,878,512 B1 | 12/2020 | Al-Zoubi et al. |
| 10,891,694 B1 | 1/2021 | Leise et al. |
| 10,971,251 B1* | 4/2021 | Giobbi .................. G16H 10/60 |
| 2002/0022976 A1 | 2/2002 | Hartigan |
| 2005/0276401 A1 | 12/2005 | Madill et al. |
| 2006/0212195 A1 | 9/2006 | Veith et al. |
| 2006/0253351 A1 | 11/2006 | Keaney |
| 2007/0185743 A1 | 8/2007 | Jinks |
| 2008/0255722 A1 | 10/2008 | McClellan et al. |
| 2009/0024419 A1 | 1/2009 | McClellan et al. |
| 2011/0090075 A1 | 4/2011 | Armitage et al. |
| 2011/0106370 A1 | 5/2011 | Duddle et al. |
| 2011/0161116 A1 | 6/2011 | Peak et al. |
| 2011/0213628 A1 | 9/2011 | Peak et al. |
| 2011/0320492 A1 | 12/2011 | Inghelbrecht |
| 2012/0029945 A1 | 2/2012 | Altieri et al. |
| 2012/0053965 A1* | 3/2012 | Hellman ................ G06Q 40/00 705/4 |
| 2012/0066007 A1 | 3/2012 | Ferrick et al. |
| 2014/0063232 A1 | 3/2014 | Fairfield et al. |
| 2014/0129261 A1 | 5/2014 | Bothwell et al. |
| 2014/0368601 A1 | 12/2014 | deCharms |
| 2015/0006205 A1 | 1/2015 | Chase et al. |
| 2015/0170112 A1 | 6/2015 | DeCastro |
| 2015/0310476 A1 | 10/2015 | Gadwa |
| 2015/0332283 A1 | 11/2015 | Witchey |
| 2016/0048923 A1 | 2/2016 | Maher et al. |
| 2016/0171619 A1 | 6/2016 | Besman et al. |
| 2016/0217532 A1 | 7/2016 | Slavin |
| 2016/0224949 A1 | 8/2016 | Thomas et al. |
| 2016/0358135 A1 | 12/2016 | Liao et al. |
| 2016/0378943 A1 | 12/2016 | Vallee |
| 2017/0034197 A1 | 2/2017 | Daniel et al. |
| 2017/0046526 A1 | 2/2017 | Chan et al. |
| 2017/0046651 A1 | 2/2017 | Lin et al. |
| 2017/0046792 A1 | 2/2017 | Haldenby et al. |
| 2017/0053461 A1 | 2/2017 | Pal et al. |
| 2017/0075941 A1 | 3/2017 | Finlow-Bates |
| 2017/0091397 A1* | 3/2017 | Shah .................... H04L 63/107 |
| 2017/0124556 A1 | 5/2017 | Seger, II |
| 2017/0161439 A1* | 6/2017 | Raduchel .............. H04W 12/06 |
| 2017/0177898 A1* | 6/2017 | Dillenberger ......... H04L 9/3236 |
| 2017/0220998 A1* | 8/2017 | Horn ..................... G06Q 50/01 |
| 2017/0300627 A1* | 10/2017 | Giordano ............... G16H 10/60 |
| 2017/0372431 A1 | 12/2017 | Perl et al. |
| 2018/0018723 A1 | 1/2018 | Nagla et al. |
| 2018/0040040 A1 | 2/2018 | Lane et al. |
| 2018/0046992 A1 | 2/2018 | Hanrahan et al. |
| 2018/0101848 A1 | 4/2018 | Castagna et al. |
| 2018/0165416 A1* | 6/2018 | Saxena ............... G06F 21/6245 |
| 2018/0218455 A1 | 8/2018 | Kolb et al. |
| 2018/0247376 A1 | 8/2018 | Sharma et al. |
| 2018/0267539 A1 | 9/2018 | Shih |
| 2018/0276054 A1 | 9/2018 | Furuichi et al. |
| 2018/0308072 A1* | 10/2018 | Smith ................ G06Q 20/0655 |
| 2019/0019186 A1 | 1/2019 | Falah et al. |
| 2019/0080392 A1 | 3/2019 | Youb et al. |
| 2019/0197620 A1 | 6/2019 | Jayaram et al. |
| 2019/0318816 A1* | 10/2019 | Witchey ................. G06Q 10/10 |
| 2019/0354966 A1 | 11/2019 | Himura et al. |
| 2019/0392437 A1 | 12/2019 | Castagna et al. |
| 2019/0392438 A1 | 12/2019 | Rice |
| 2020/0058071 A1 | 2/2020 | Yang |
| 2020/0065763 A1 | 2/2020 | Rosinzonsky et al. |
| 2020/0177373 A1 | 6/2020 | Komandur et al. |
| 2020/0226677 A1 | 7/2020 | Dhawan et al. |
| 2020/0250753 A1 | 8/2020 | Blount |
| 2020/0272966 A1 | 8/2020 | Kirkegaard |
| 2020/0279328 A1 | 9/2020 | Zhiri et al. |
| 2020/0341971 A1 | 10/2020 | Krishnaswamy et al. |
| 2020/0394321 A1 | 12/2020 | Ramos et al. |
| 2020/0394322 A1 | 12/2020 | Ramos et al. |
| 2020/0409937 A1 | 12/2020 | Wang et al. |
| 2021/0065293 A1 | 3/2021 | Sigler et al. |
| 2021/0090037 A1 | 3/2021 | Dowding |
| 2021/0174442 A1 | 6/2021 | Trudeau et al. |

OTHER PUBLICATIONS

Azaria et al.: "MedRec: Using Blockchain for Medical Data Access and Permission Management", 2016 2nd International Conference on Open and Big Data (OBD), Vienna, Austria, Aug. 2016 (Year: 2016).*

U.S. Appl. No. 15/870,292, Nonfinal Office Action, dated Dec. 31, 2019.

U.S. Appl. No. 15/87,350, Nonfinal Office Action, dated Oct. 10, 2019.

U.S. Appl. No. 15/870,364, Nonfinal Office Action, dated Oct. 9, 2019.

U.S. Appl. No. 15/870,371, Nonfinal Office Action, dated Aug. 28, 2019.

Van Oerle et al., "Distributed ledger technology for the financial industry, Blockchain Administration 3.0", White Paper, Robeco (May 2016).

Blockchain in the insurance sector. Retrieved from the Internet at: <URL: https://www.pwc.co.uk (2016).

HashCoin Uses Emercoin Blockchain for Vehicle Registration and Tracking. Retrieved from the internet at: <URL: https://cointelegraph.com/news/hashcoin-uses-emercoin-blockchain-for-vehicle-registration-and-tracking (2018).

Haber and Stornetta, "How to Time-Stamp a Digital Document", Bellcore, NJ (1991).

Mazieres and Shasha, "Building secure file systems out of Byzantine storage", NYU (2002).

BlockstreetHQ Team, "Before Blockchain, There was Distributed Ledger Technology BlockstreetHQ," Medium.com (2018).

Sneakernet, definition, Wikipedia. Retrieved from the Internet at: <https://en.wikipedia.org/wiki/Sneakernet> (2020).

File Transfer Protocol, definition/history/overview, Wikipedia. Retrieved from the Internet at: <https://en.wikipedia.org/wiki/File Transfer Protocol> (2020).

Distribution File system overview. Retrieved from the Internet at: <http://www.cse.chalmers.se/~tsigas/Courses/DCDSeminar/Files/afs_report.pdf> (2020).

Authors et al.: Disclosed Anonymously, "Mechanism to Preserve Audit History Record for Insurance Claim Using Blockchain Smart Contract", An IP.com Prior Art Database Technical Disclosure (2016).

(56) References Cited

OTHER PUBLICATIONS

C.L.U.E.® Personal Property, "How to Read Your Rreport", ChoicePoint (1999).

Goodman et al., "CLUE Reports Comprehensive Loss Underwriting Reports", CLUE, Apr. 1, 2003.

"Blockchain in the insurance sector," Web page <https://www.pwc.co.uk/financialservices/fintech/assets/blockchain-in-insurance.pdf>, 2 pages, dated Aug. 7, 2016 by the Internet Archive Wayback Machine; retrieved from the Internet Archive Wayback Machine <http://web.archive.org/web/*/https://www.pwc.co.uk/financial-services/fintech/assets/blockchain-in-insurance.pdf> on Apr. 12, 2021.

Cointelegraph, "HashCoin Uses Emercoin Blockchain For Vehicle Registration and Tracking," Retrieved from the Internet at: <https://cointelegraph.com/news/hashcoin-uses-emercoin-blockchain-forvehicle-registration-and-tracking> dated Dec. 8, 2016.

\* cited by examiner

Loss History Report 680

Date of Order: XX/YY/ZZ — 681

Date of Receipt: XX/YY/ZZ — 682

Reference Number: 12345 — 683

Recap: 4 claims reported — 684

Search
Name: John Doe
Date of Birth: XX/YY/ZZ
SSN: 123-45-6789
Sex: M
Address: 123 Broadway Ave, Chicago, IL
Telephone
— 685

*Fig. 6C*

DISTRIBUTED LEDGER SYSTEM FOR MANAGING MEDICAL RECORDS

CROSS-REFERENCE TO RELATED APPLICATIONS

The present disclosure claims the benefit of (i) U.S. Provisional Patent Application No. 62/500,049, titled "Distributed Ledger Systems," filed on May 2, 2017; (ii) U.S. Provisional Patent Application No. 62/500,326, titled "Distributed Ledger System," filed on May 2, 2017; (iii) U.S. Provisional Patent Application No. 62/508,133, titled "Distributed Ledger System for Managing Smart Home Data, Vehicle Data, Insurance Claim Payouts, and/or Insurance Carrier Discovery," filed on May 18, 2017; (iv) U.S. Provisional Patent Application No. 62/545,262, titled "Distributed Ledger System for Managing Loss Histories," filed on Aug. 22, 2017; (v) U.S. Provisional Patent Application No. 62/548,668, titled "Distributed Ledger System for Managing Vehicle Sensor Data Utilized to Develop Collision Profiles," filed on Aug. 22, 2017; (vi) U.S. Provisional Patent Application No. 62/548,679, titled "Distributed Ledger System for Use with Vehicle Sensor Data and Usage Based Systems," filed on Aug. 22, 2017; (vii) U.S. Provisional Patent Application No. 62/548,682, titled "Distributed Ledger System for Managing Medical Records," filed on Aug. 22, 2017; (viii) U.S. Provisional Patent Application No. 62/548,692, titled "Distributed Ledger System for Insurance Record Management Systems," filed on Aug. 22, 2017; (ix) U.S. Provisional Patent Application No. 62/548,741, titled "Distributed Ledger System for Smart Home Data," filed on Aug. 22, 2017; (x) U.S. Provisional Patent Application No. 62/548,700, titled "Distributed Ledger System for Managing Smart Vehicle Data," filed on Aug. 22, 2017; (xi) U.S. Provisional Patent Application No. 62/548,731, titled "Distributed Ledger System for Claim Payouts," filed on Aug. 22, 2017; and (xii) U.S. Provisional Patent Application No. 62/548,748, titled "Distributed Ledger System for Carrier Discovery," filed on Aug. 22, 2017; the entire disclosures of which are expressly incorporated herein by reference.

TECHNICAL FIELD

Systems and methods are disclosed with respect to using a distributed ledger for managing medical records.

BACKGROUND

Generally speaking, companies may utilize centralized databases or servers for a number of purposes. For example, medical records are often held by a multitude of different institutions, each of which maintains its own centralized database including an incomplete record of a patient's medical history (e.g., relating to only a certain period of time or to certain specialty procedures). These medical records held by institutions are often not synchronized, and may not be consistent. Further, the medical records may not be readily accessible by patients or by third parties that might otherwise be authorized to access the medical records.

BRIEF SUMMARY

In one aspect, a computer-implemented method for tracking medical histories may include (1) configuring or implementing a plurality of servers, each of the plurality of servers maintaining a copy of a distributed ledger; (2) creating, at the distributed ledger, a medical history for a patient; and (3) when a request for a medical history report for the patient is received, generating the medical history report by retrieving the medical history for the patient from a copy of the distributed ledger maintained by one of the plurality of servers. Creating the medical history for the patient may include performing one or more of the following when an insurance claim involving the patient is filed: (i) generating, at a first server from the plurality of servers, a transaction record including data representing the filed insurance claim and data representing a medical profile for the patient; (ii) proposing the transaction record to one or more other servers from the plurality of servers; (iii) performing, via the plurality of servers, a consensus analysis of the transaction record utilizing a consensus mechanism; and/or (iv) when the consensus analysis indicates that the plurality of servers have formed a consensus, storing the transaction record at the distributed ledger by storing the transaction record to each copy of the distributed ledger at the plurality of servers. The method may include additional, less, or alternate actions, including those discussed elsewhere herein.

Advantages will become more apparent to those of ordinary skill in the art from the following description of the preferred aspects, which have been shown and described by way of illustration. As will be realized, the present aspects may be capable of other and different aspects, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

There are shown in the drawings arrangements which are presently discussed, it being understood, however, that the present embodiments are not limited to the precise arrangements and instrumentalities shown, wherein:

FIG. 6C is an exemplary loss history report that may be generated by a nodes and/or client device in accordance with one aspect of the present disclosure.

Figure 1A:
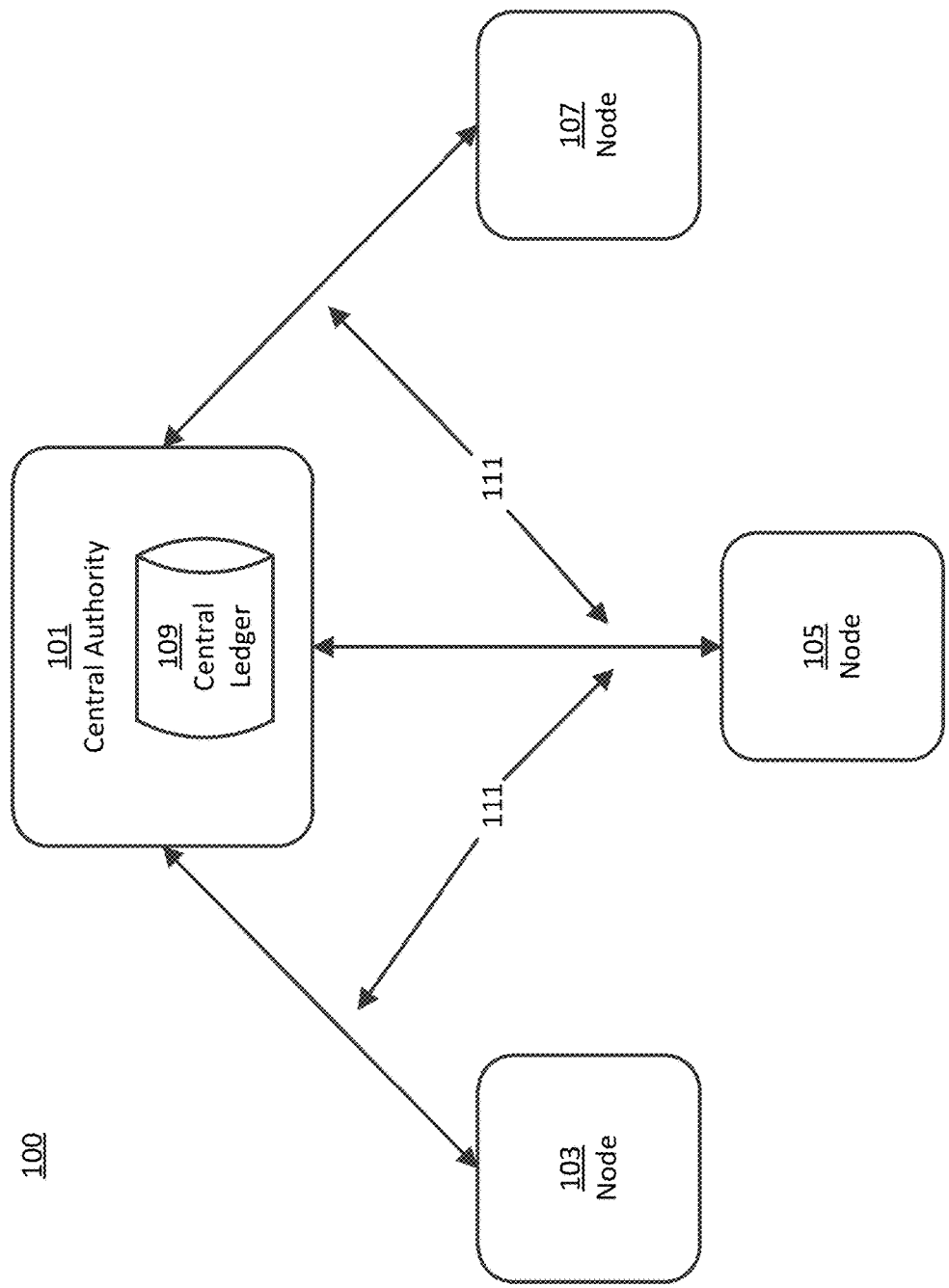
FIG. 1A depicts an exemplary database system in accordance with one aspect of the present disclosure.

The figures depict aspects of the present embodiments for purposes of illustration only. One skilled in the art will readily recognize from the following discussion that alternate aspects of the structures and methods illustrated herein may be employed without departing from the principles of the invention described herein.

DETAILED DESCRIPTION

The present embodiments relate to, inter alia, systems and methods for using a distributed ledger to record information related to processes and services in the healthcare, automotive, and real estate industries. For example, a distributed ledger may be used to manage: (i) data associated with loss history reports (for either individuals or insured assets, such as real estate, vehicles, personal articles, etc.); (ii) data associated with sensor-based insurance systems; (iii) data associated with medical record systems; and/or (iv) data associated with insurance record management systems. In some embodiments, the distributed ledger is a blockchain system. The systems and methods described herein allow for using a distributed ledger which gives the option for private information, and permissioned participants in the blockchain. In particular, the systems and methods allow for a distributed consensus amongst businesses, consumers, and authorities, as to the validity of information and transactions stored on the distributed ledger.

The above listed examples, and disclosed systems and methods, may use an application of distributed ledgers, where each new block may be cryptographically linked to the previous block in order to form a "blockchain."

A blockchain is a way of achieving a distributed consensus on the validity or invalidity of information. As opposed to using a central authority, a blockchain is a distributed database, or ledger, in which transactional records are maintained at each node of a peer to peer network. Commonly, the distributed ledger is comprised of groupings of "transactional records" (sometimes simply referred to as "transactions") bundled together into a "block." Generally speaking, each "transaction" or "transactional record" is a record of an update or change made to the distributed ledger. The nature of the information included in each transactional record generally depends on the particular implementation of a given distributed ledger, and on the information the distributed ledger is intended to track.

When a change to the distributed ledger is made (e.g., when a new transaction and/or block is created), each node must form a consensus as to how the change is integrated into the distributed ledger. Upon consensus, the agreed upon change is pushed out to each node so that each node maintains an identical copy of the updated distributed ledger. Any change that does not achieve a consensus is ignored. Accordingly, unlike a traditional system which may use a central authority, a single party cannot unilaterally alter the distributed ledger. This inability to modify past transactions lead to blockchains being generally described as trusted, secure, and immutable.

Some blockchains may be deployed in an open, decentralized, and permissionless manner meaning that any party may view information, submit new information, or join the blockchain as a node responsible for confirming information. This open, decentralized, and permissionless approach to a blockchain has limitations. As an example, these blockchains may not be good candidates for interactions that require information to be kept private, such as information related to a vehicle lifecycle process, or for interactions that require all participants to be vetted prior to their participation.

In any event, to create a new block, each transaction within a block may be assigned a hash value (i.e., an output of a cryptographic hash function, such as SHA-256 or MD5). These hash values may then be combined together utilizing data storage and cryptographic techniques (e.g., a Merkle Tree) to generate a hash value representative of the entire new block, and consequently the transactions stored in the block. This hash value may then be combined with the hash value of the previous block to form a hash value included in the header of the new block, thereby cryptographically linking the new block to the blockchain. To this end, the precise value utilized in the header of the new block may be dependent on the hash value for each transaction in the new block, as well as the hash value for each transaction in every prior block.

According to certain aspects disclosed herein, information stored in blockchains may be trusted, because the hash value generated for the new block and a nonce value (an arbitrary number used once) are used as inputs into a cryptographic puzzle. The cryptographic puzzle may have a difficulty set by the nodes connected to the blockchain network, or the difficulty may be set by administrators of the blockchain network. In one example of the cryptographic puzzle, a solving node uses the hash value generated for the new block and repeatedly changes the value of the nonce until a solution for the puzzle is found. For example, finding the solution to the cryptographic puzzle may involve finding the nonce value that meets certain criteria (e.g., the nonce value begins with five zeros).

When a solution to the cryptographic puzzle is found, the solving node publishes the solution and the other nodes then verify that the solution is valid. Since the solution depends on the particular hash values for each transaction within the blockchain, if the solving node attempted to modify any transaction stored in the blockchain, the solution would not be verified by the other nodes. More specifically, if a single node attempts to modify a prior transaction within the blockchain, a cascade of different hash values may be generated for each tier of the cryptographic combination technique. This results in the header for one or more blocks being different than the corresponding header(s) in every other node that did not make the exact same modification.

Exemplary Database & Distributed Ledger

FIG. 1A depicts an exemplary central authority database system 100 in accordance with one aspect of the present disclosure. FIG. 1A includes a central authority 101; a plurality of nodes 103, 105, and 107; a central ledger 109; and a plurality of network connections 111. In one exemplary operation of the database system 100, one of the nodes, for example node 103, issues a request to the central authority 101 to perform an action on data stored in the central ledger 109. This request may be a request to create, read, update, or delete data that is stored in the central ledger 109.

In such an example, the central authority 101 receives the request, processes the request, makes any necessary changes to the data stored in the central ledger 109, and informs the requesting node (node 103) of the status of the request. The central authority 101 may also send out status updates to the other nodes on the network about the change made, if any, to the data by node 103. In the database system 100, all interaction with the data stored in the central ledger 109 occurs through the central authority 101. In this way, the central authority functions as a gatekeeper of the data.

Accordingly, the central authority 101 may operate as a single point of entry for interacting with the data, and consequently the central authority 101 is a single point of failure for the entire database system 100. As such, if the central authority 101 is not accessible to the nodes in the database system 100, then the data stored in the central ledger 109 is not accessible. In another example, each individual node may keep its own databases and may periodically send a copy of its database to the central authority 101, where the received databases are reconciled to form a single cohesive record of the data stored in the central ledger 109.

Figure 1B:
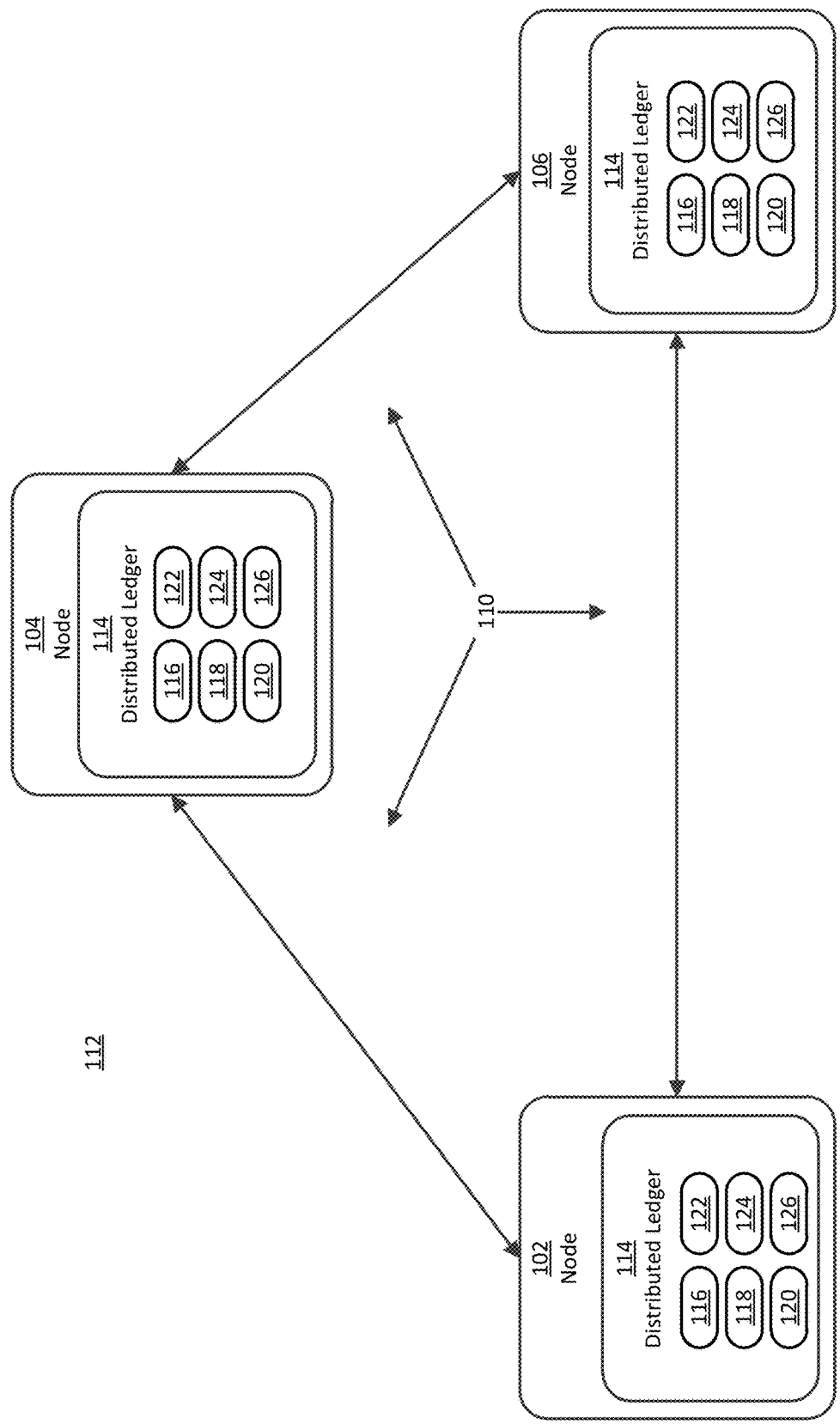
FIG. 1B depicts an exemplary distributed ledger system in accordance with one aspect of the present disclosure.

Conversely, FIG. 1B depicts an exemplary distributed ledger system 112 in accordance with an aspect of the present disclosure. An example of a distributed ledger system 112 is the blockchain system described above. FIG. 1B includes a plurality of nodes 102, 104, and 106; a distributed ledger 114; and a plurality of network connections 110. In the distributed ledger system 112, each node keeps a copy of the distributed ledger 114.

Each copy of the distributed ledger 114 maintains a copy of a plurality of transactions 116-126 tracked in the distributed ledger 114. Generally speaking, each of the transactions 116-126 (sometimes referred to as a "transactional records" or "transaction records") is a record of an update or change made to the distributed ledger 114. The nature of the information included in each transactional record 116-126 generally depends on the particular implementation of the distributed ledger 114, and on the information the distributed ledger 114 is intended to track.

As changes are made to the distributed ledger 114, each node 102-106 updates its copy of the distributed ledger 114. A consensus mechanism (sometimes referred to as a consensus protocol) may be used by the nodes in the distributed ledger system 112 to decide when it is appropriate to make changes to the distributed ledger 114. Example consensus mechanisms that may be used by the distributed ledger 114 include: proof of work, proof of stake, proof of activity, proof of burn, proof of capacity, and/or proof of elapsed time. Therefore, each node has its own copy of the distributed ledger 114, which is identical to every other copy of the distributed ledger 114 stored by each other node. The distributed ledger system 112 is more robust than a central authority database system such as the system 100 shown in FIG. 1A, because the distributed ledger system 112 is decentralized and no single point of failure exists.

The system 112 and distributed ledger 114 may be implemented using a number of different blockchain protocols, depending on the embodiment. Example blockchain protocols that may be implemented include: Hyperledger Fabric, Ethereum, Corda, Ripple, ZCash, and Sawtooth. For example, the method 600 described with reference to FIG. 6A may be implemented to track loss history using the distributed ledger 114 in one embodiment in which the distributed ledger 114 is configured to utilize the Hyperledger Fabric protocol.

Figure 1C:
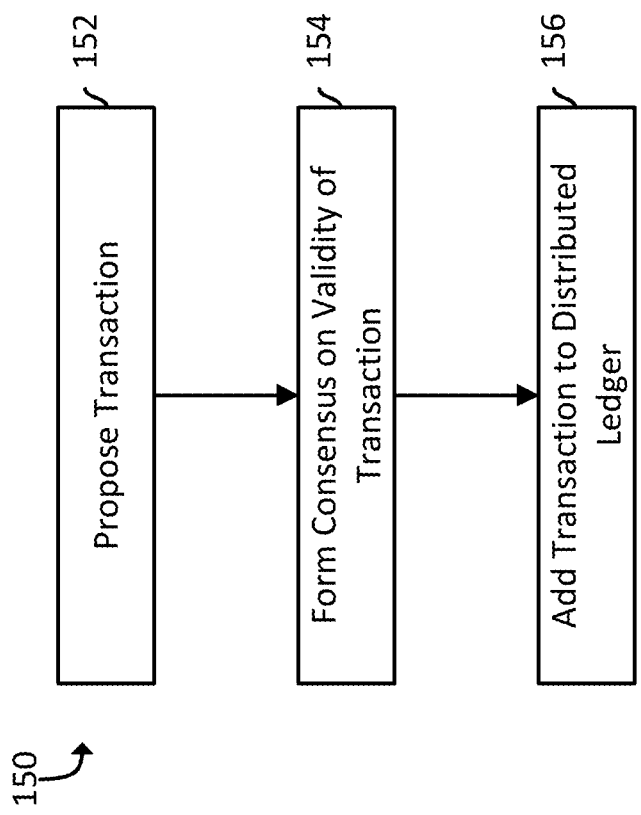
FIG. 1C depicts an exemplary method for adding a transaction to a distributed ledger in accordance with one aspect of the present disclosure.

FIG. 1C is a flow chart of an exemplary computer-implemented method 150 for adding a transaction to the distributed ledger 114 in accordance with one aspect of the present disclosure. The method 150 may be implemented, in whole or in part, by the nodes 102-106 in the system 112 shown in FIG. 1B, and may be saved to a memory of one or more of the nodes as one or more instructions or routines executable by a processor.

The method 150 begins when a node proposes a transaction (block 152). The nature of the transaction depends on the implementation. In one embodiment, the ledger 114 tracks loss history for properties and each transaction represents a claim filed against a particular property. In such an embodiment, a new transaction might be proposed when an insurance company receives or completes a claim filed against a particular property. The transaction might include data about the property (e.g., property type, address of a home, make and model of a vehicle, etc.), owner (e.g., name, social security number, etc.), and/or claim (damage type, estimated loss, claim payout amount, etc.).

One or more other nodes in the system 112 may receive the proposed transaction and attempt to form a consensus in order to verify the validity of the transaction (block 154). The nodes may utilize a proof of work consensus protocol such as that already described. If the nodes are unable to reach consensus, the transaction is not added to the ledger 114. When the nodes reach consensus, the transaction is added to the distributed ledger 156. That is, a copy of the transaction is added to each copy of the ledger 114 held at each node 102-106. Accordingly, the nodes 102-106 are able to maintain identical copies of the ledger 114, thus maintaining consistency and accuracy of the ledger 114 without a single central authority.

Exemplary Transaction Flow & Block Propagation Flow

Figure 2A:
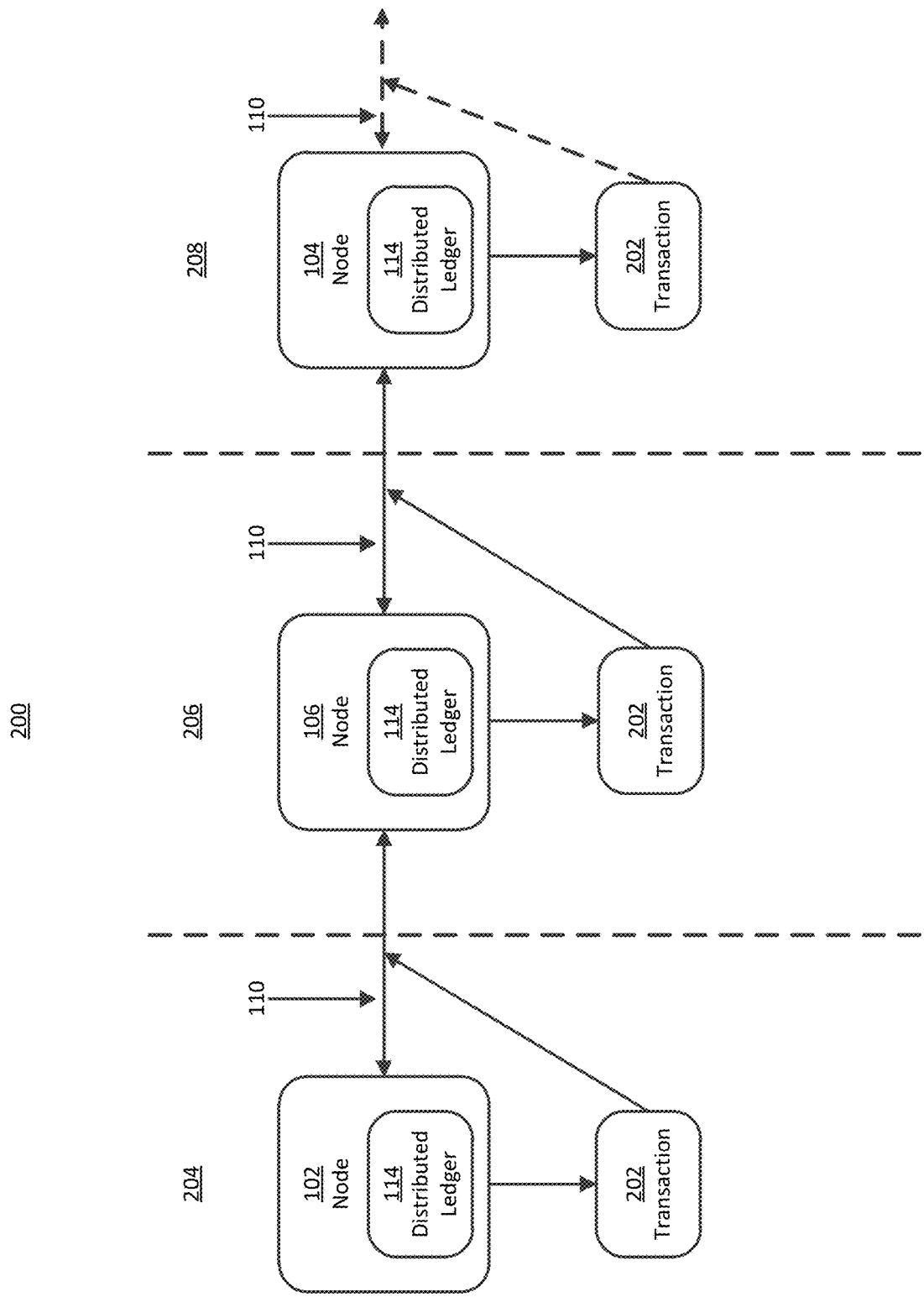
FIG. 2A depicts an exemplary transaction flow in accordance with one aspect of the present disclosure.

FIG. 2A depicts an exemplary transaction flow 200 in accordance with one aspect of the present disclosure. FIG. 2A includes a transactional record ("transaction") 202; three different time frames 204, 206, and 208; the nodes 102-106; the network connections 110; and the distributed ledger 114. The transaction flow 200 may represent a sequential flow of the transaction 202 through a network (such as the network depicted in FIG. 1B).

In the shown example, the node 102 generates the transaction 202 at time 204. The transaction 202 may include data that is stored in the distributed ledger 114 at the node 102, or may include data received by the node 102 from outside the distributed ledger 114. The node 102 may transmit the newly generated transaction 202 to node 106 via the network connection 110.

At time 206, the node 106 receives the transaction 202, and confirms that the information contained therein is correct. If the information contained in the transaction 202 is not correct, the node 106 may reject the transaction and not propagate the transaction 202 through the system. If the information contained in the transaction 202 is correct, the node 106 may transmit the transaction 202 to the node 104.

At time 208, the node 104 may receive the transaction 202 and may confirm or reject the transaction 202. In some embodiments, the node 104 may not transmit the confirmed transaction 202, because there are no further nodes to transmit to, or all the nodes in the network have already received transaction 202.

In some embodiments, at any of time frames 204, 206, or 208, any of the nodes may add the confirmed transaction 202 to their copy of the distributed ledger 114, or to a block of transactions stored in the distributed ledger 114. In some embodiments, confirming the transaction 202 includes checking cryptographic key-pairs for participants involved in the transaction 202. Checking the cryptographic key-pairs may follow a method laid out by a consensus protocol, such as the consensus protocol discussed in FIG. 1B.

Figure 2B:
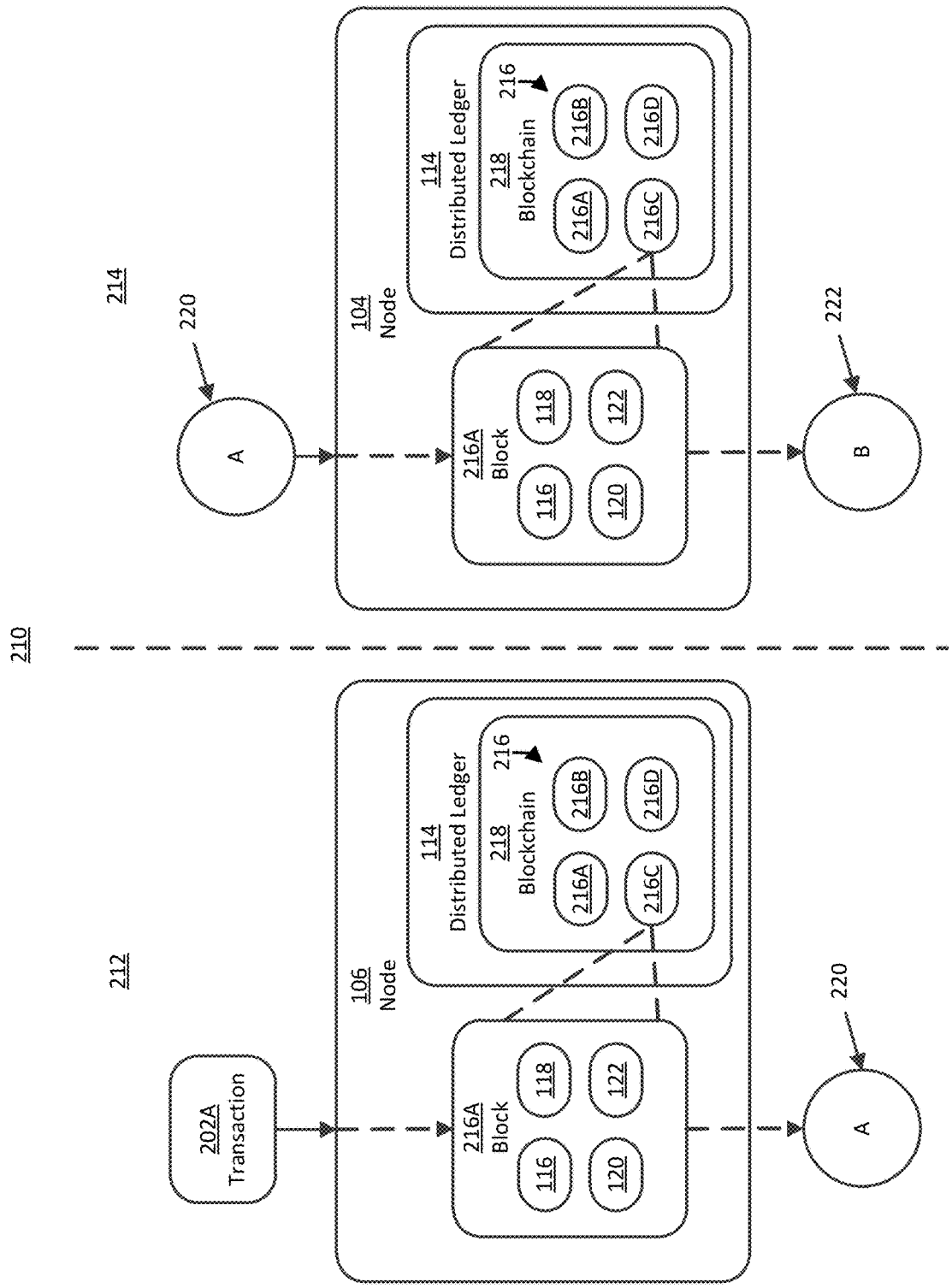
FIG. 2B depicts an exemplary block propagation flow in accordance with one aspect of the present disclosure.

FIG. 2B depicts an exemplary block propagation flow 210 in accordance with one aspect of the present disclosure. FIG. 2B includes two time frames 212 and 214; the node 106 and the node 104; the transactions 116-122; a set of blocks of transactions 216A-216D; the distributed ledger 114; and a blockchain 218. The block propagation flow 210 may follow the blockchain system described above, or may follow another blockchain propagation algorithm.

The block propagation flow 210 may begin with the node 106 receiving the transaction 116 at time 212. When node 106 confirms that the transaction 116 is valid, the node 106 may add the transaction 116 to the block 216A (which may be newly generated). As part of adding the transaction 116 to the block 216A, node 106 may solve a cryptographic puzzle and include the solution in the newly generated block 216A as proof of the work done to generate the block 216A. This proof of work may be similar to the proof of work described above which utilizes guessing a nonce value. In other embodiments, the transaction 116 may be added to a pool of transactions until enough transactions exist to form a block. Node 106 may transmit the newly created block 216A to the network at 220. Before or after propagating the block 216A, node 106 may add the block 216A to its copy of the blockchain 218.

At time 214, node 104 may receive the block 216A. Node 104 may verify that the block 216A is valid by checking the solution to the cryptographic puzzle provided in the block 216A. If the solution is accurate, then the node 104 may add the block 216A to its blockchain 218 and transmit the block 216A to the rest of the network at 222.

In one embodiment, one or more transactions 202 or events may relate to: smart contracts, loss history and loss history reports, insurance claims, vehicle sensor data, medical records, and/or insurance records.

Figure 2C:
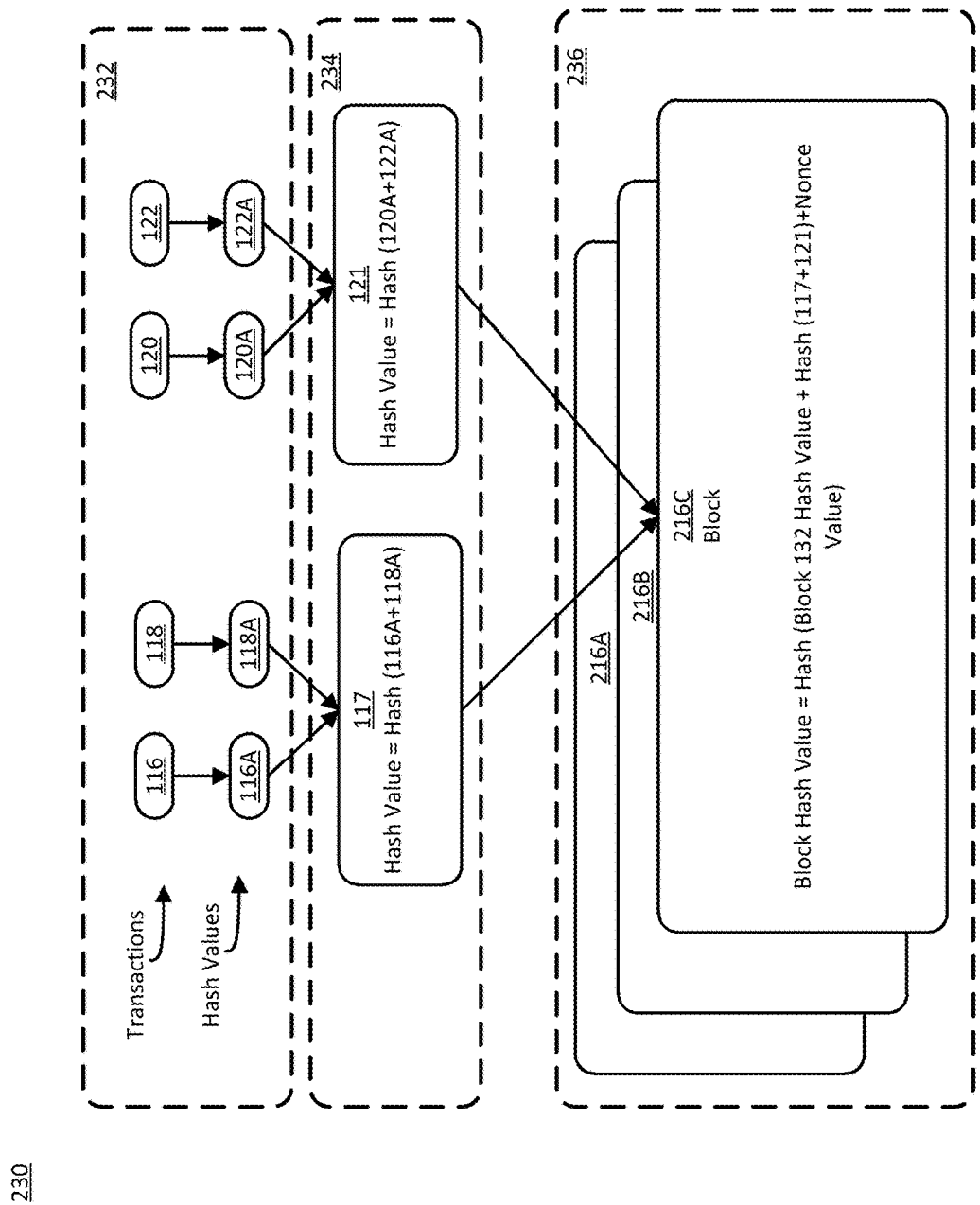
FIG. 2C depicts an exemplary computer-implemented method for generating a block in a blockchain in accordance with one aspect of the present disclosure.

FIG. 2C depicts an exemplary method 230 for generating the block 216C shown in FIG. 2B, according to one embodiment. The method 230 may be implemented by a processor of one or more of the nodes 102-106, and may be implemented as part of a consensus mechanism. It will be understood that the method 230 is exemplary, and not every embodiment implements the method 230.

In the method 230, a processor generates hash values 116A-122A for each of the transactions 116-122, using data associated with each of the transactions 116-122 as inputs for a hash function (step 232). The processor then generates a hash value 117 using the hash values 116A and 118A as inputs for the hash function, and a hash value 121 using the hash values 120A and 122A as inputs for the hash function (step 234). Finally, when generating block 216C, a hash for block 216 is generated using as inputs: a hash value of the "chained" block 216B, the hash vales 117 and 121, and a nonce value (step 236). Because every other node may have access to the block 216B and to the transactions 116-122, when a node publishes that a cryptographic puzzle has been solved utilizing the nonce value, the other nodes can confirm whether or not the solution is valid (because a change to any transaction 116-122, or to any transaction in block 216B, or to the nonce value, will result in a different hash value for block 216C).

Exemplary Sequence Diagram

Figure 3:
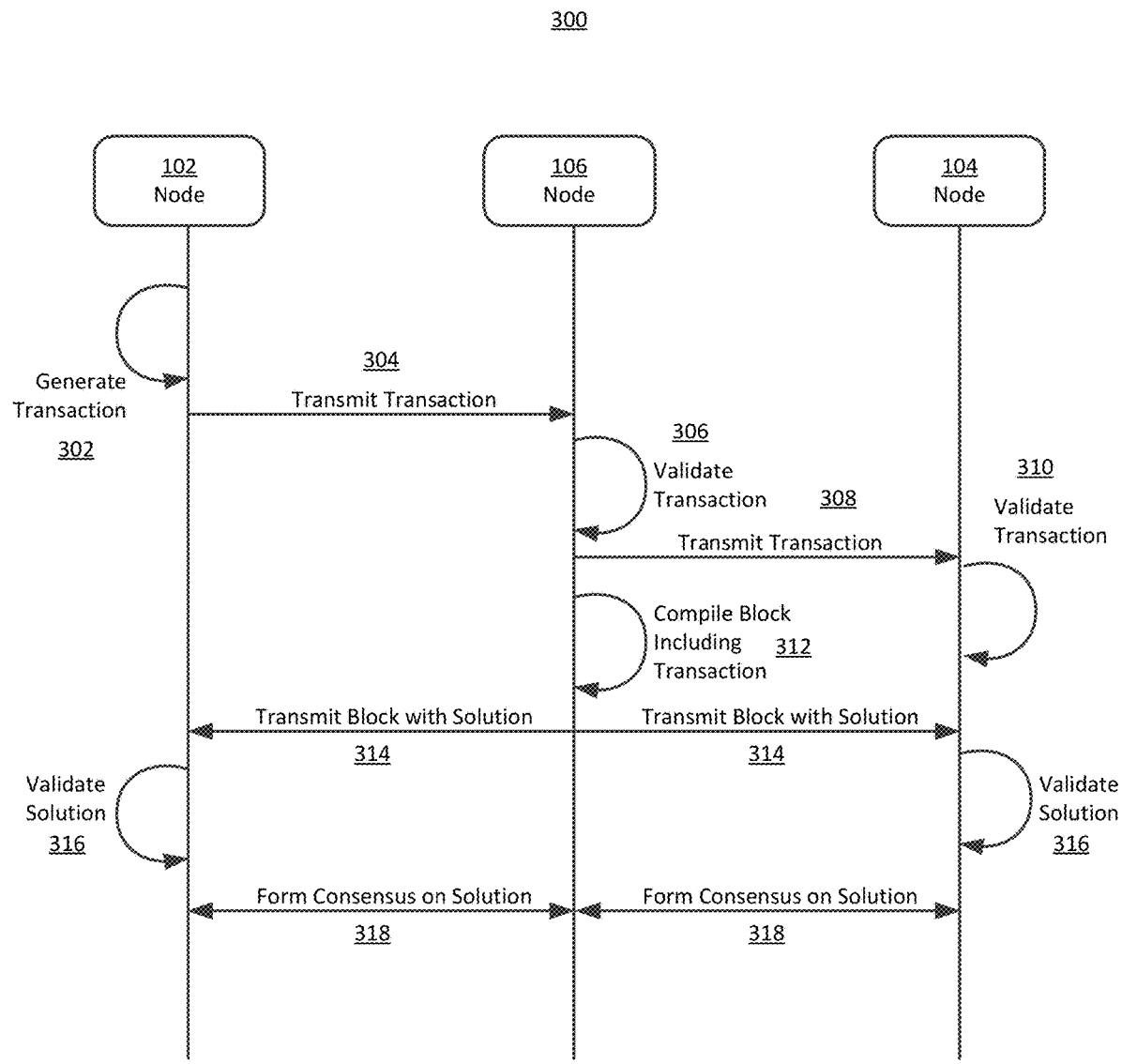
FIG. 3 depicts an exemplary sequence diagram in accordance with one aspect of the present disclosure.

FIG. 3 depicts an exemplary sequence diagram 300 in accordance with one aspect of the present disclosure. FIG. 3 includes the set of nodes 102, 104, and 106. At time 302, the node 102 may generate a transaction. At time 304, the transaction may be transmitted from the node 102 to the node 106. At time 306, the node 106 may validate the transaction. At time 308, if the transaction is valid, the node 106 may transmit the transaction to node 104. At time 310, node 104 may validate the transaction. At time 312, the node 106 may compile a block including the validated transaction. Compiling a block may include generating a solution to a cryptographic puzzle and linking the block to other blocks, as described in the embodiments above. At time 314, once the block is compiled, the node 106 may transmit the block with the solution to both the node 102 and the node 104.

At time 316, both nodes may validate the solution to the block. Verifying may include checking a cryptographic key-pair as described above. At time 318, the three nodes form a consensus that the solution is valid. Accordingly, in the shown example, all the nodes have formed a consensus on the blocks of transactions stored by all the nodes.

Exemplary Node

Figure 4:
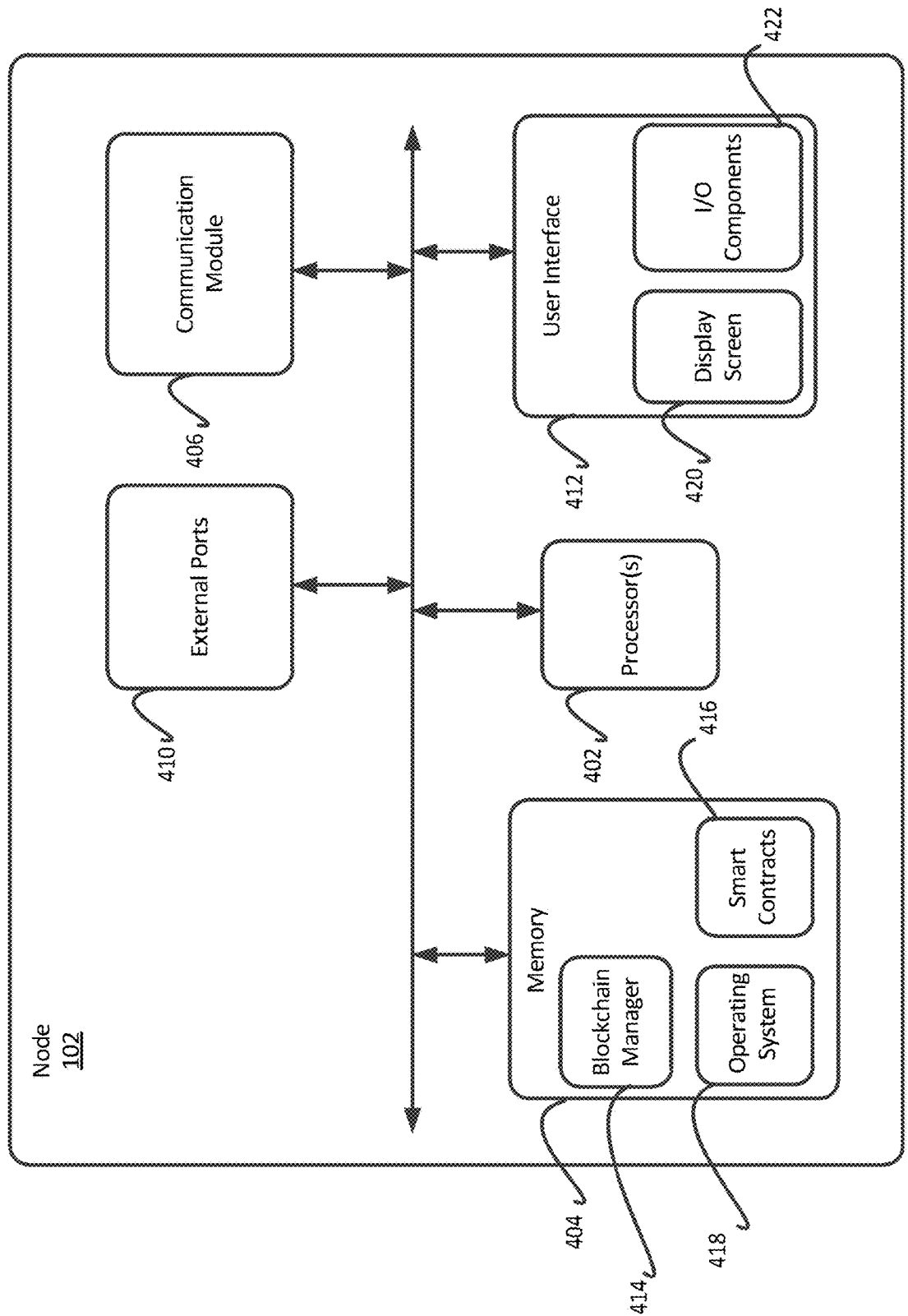
FIG. 4 depicts an exemplary node in accordance with one aspect of the present disclosure.

FIG. 4 is a block diagram of the node 102, according to one embodiment. It will be understood that the nodes 104 and 106 may perform one or more of the functions that the node 102 is capable of performing, and may include one or more of the components included in the node 102. The node 102 may utilize the decentralized system 112 described with respect to FIG. 1B, the flows 200 and 210 of transactions and blocks described in FIGS. 2A and 2B, and/or the blockchain system 500 described below with reference to FIG. 5.

The node 102 includes one or more of the following: at least one processor 402, memory 404, a communication module 406, a set of applications 408, one or more external ports 410, a user interface 412, a blockchain manager 414, smart contracts 416, an operating system 418, a display screen 420, and input/output components 422. In some embodiments, the node 102 may generate a new block of transactions using the blockchain manager 414. Similarly, the node 102 may use the blockchain manager 414 in conjunction with the smart contracts 416 stored in memory 404 to execute the functionality disclosed herein.

In some embodiments, the smart contracts 416 operate independent of the blockchain manager 414 or other applications. In some embodiments, the node 102 does not include one or more of the blockchain manager 414 or the smart contracts 416. In some embodiments, the node 102 may have additional or less components than what is described. The smart contracts may relate to, or be associated with, insureds and/or insured assets, including smart insurance contracts, smart maintenance contracts, smart health care contracts, smart repair or upkeep contracts, etc.

The node 102, as part of a decentralized ledger system 112, or another decentralized or centralized network, may be used to handle systems that interact with and manipulate data and transactions designed for tracking loss history, vehicle sensor data, medical records, and/or insurance records.

Exemplary Blockchain System

Figure 5:
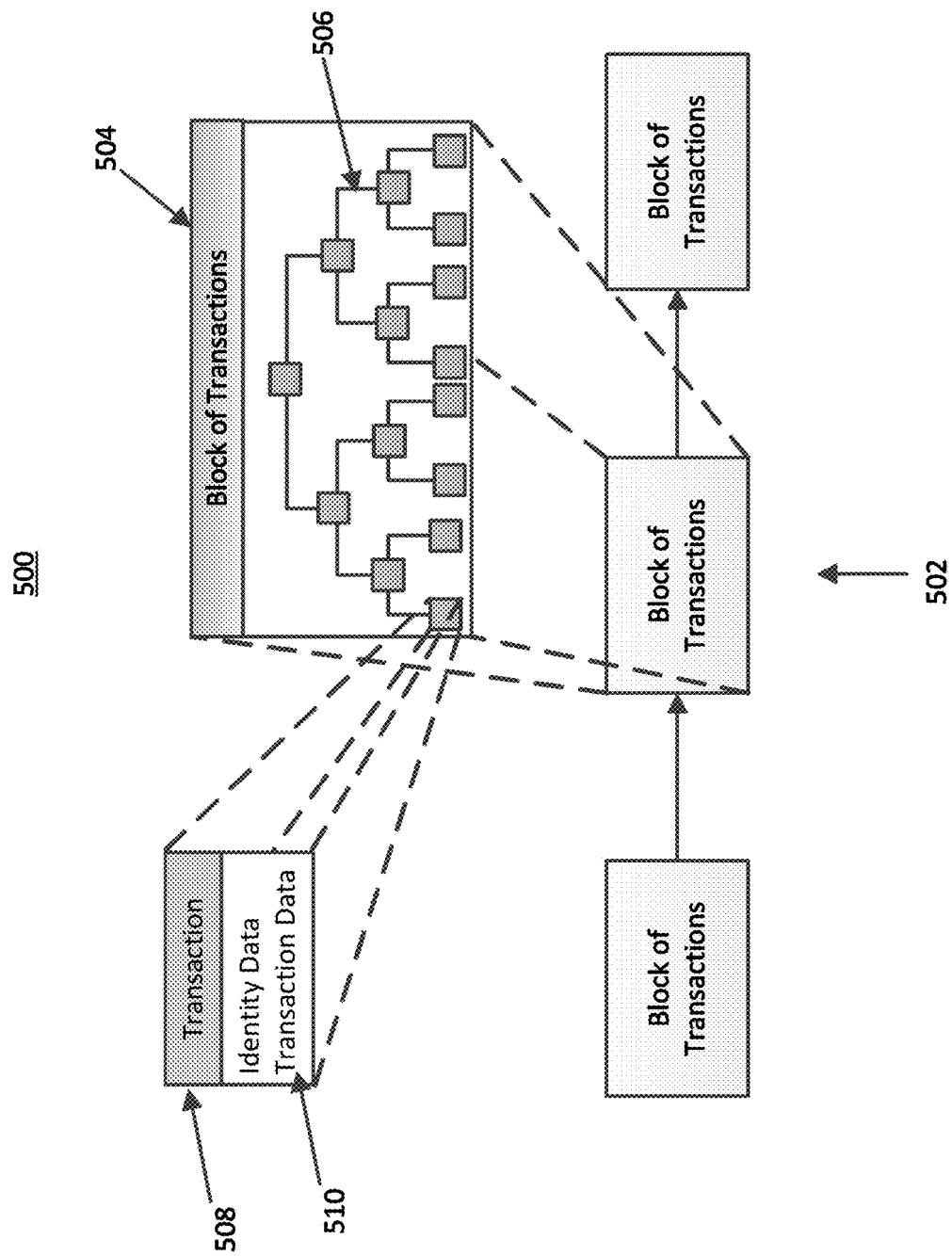
FIG. 5 depicts an exemplary blockchain in accordance with one aspect of the present disclosure.

FIG. 5 depicts an exemplary blockchain system 500 in accordance with an aspect of the present disclosure. The system 500 includes a blockchain 502 that includes one or more blocks, including a block of transactions 504. The block 504 includes a Merkle Tree 506 that includes one or more transactions, including a transaction 508 that includes data 510. The Merkle Tree 506 may be the same Merkle Tree referred to above that cryptographically links transactions together. In some embodiments, the blockchain system 500 may utilize other methods of organizing transactions in a block.

As noted, the block of transactions 504 includes the transaction 508, but may also include other transactions in some instances. In some embodiments, the block of transactions 504 has a size limit limiting the number of transactions that the block 504 may store. In one exemplary implementation, the block 504 includes a reference to a previous block of transactions that was added to the blockchain 502 prior to the block 504 being added to the blockchain 502. As such, and as described above, each block in the blockchain 502 is linked to every other block in the blockchain 502.

In some embodiments, the block of transactions 504 may organize the transactions it has received into a Merkle Tree 506 to facilitate access to the stored transactions. The transactions may be hashed using a cryptographic hash algorithm, such as the algorithms discussed above, and the hash of each transaction may be stored in the tree. As the tree is constructed, the hash of each adjacent node at the same level is hashed together to create a new node that exists at a higher level in the tree. Therefore, the root of the tree, or the node at the top of the tree, is dependent upon the hash of each transaction stored below in the tree. Each transaction 508 may include a set of data 510. The set of data 510 may include an identifier for the transaction (e.g., a unique string), and transaction data identifying the nature of the transaction and what the transactions entails.

In some embodiments, the blockchain 218 shown in FIG. 2B may be similar to the blockchain 502, and the transactions 116-126 shown in FIGS. 1B and 2B may be similar to the transaction 508. In some embodiments, the ledger 114 may share some of the functionality of the system 500, as well as the organization of blocks and transactions.

Loss History Reports

In one embodiment, a distributed ledger is utilized to track insurance claims and to generate loss history reports. The present embodiments may be configured to track all insurance claims relating to a particular person and/or property (e.g., a home, automobile, personal articles, or other insured assets), develop one or more loss histories and store them on a blockchain.

In one embodiment, the distributed ledger system 112 shown in FIG. 1B may be utilized to track insurance claims. Advantageously, such a system enables the insurance companies to eliminate the third party typically responsible for maintaining the centralized database. Multiple insurance companies may maintain a local copy of the distributed ledger 114. For example, Alpha Insurance Company ("Alpha") may maintain a local copy of the ledger 114 at the node 102, Bravo Insurance Company ("Bravo") may maintain a local copy of the ledger 114 at the node 104, and Charlie Insurance Company ("Charlie") may maintain a local copy of the ledger 114 at the node 106.

Each transaction stored at the ledger 114 may represent a filed claim, and may include data representing one or more of the following items: a unique transaction identifier; an identifier for the insured (e.g., unique identifier and/or name of the insured); an address for the insured; a birth date for the insured; a social security number for the insured; a name of the insurance company receiving the claim; an indication of the type of insurance policy held by the insured; an insurance policy number; an identifier for the type of loss (e.g., indicating fire damage, water damage, hail damage, etc.); the date of the loss; the monetary loss for the claim; the status of the claim; and information associated with one or more smart contracts, such as a smart insurance contract.

Figure 6A:
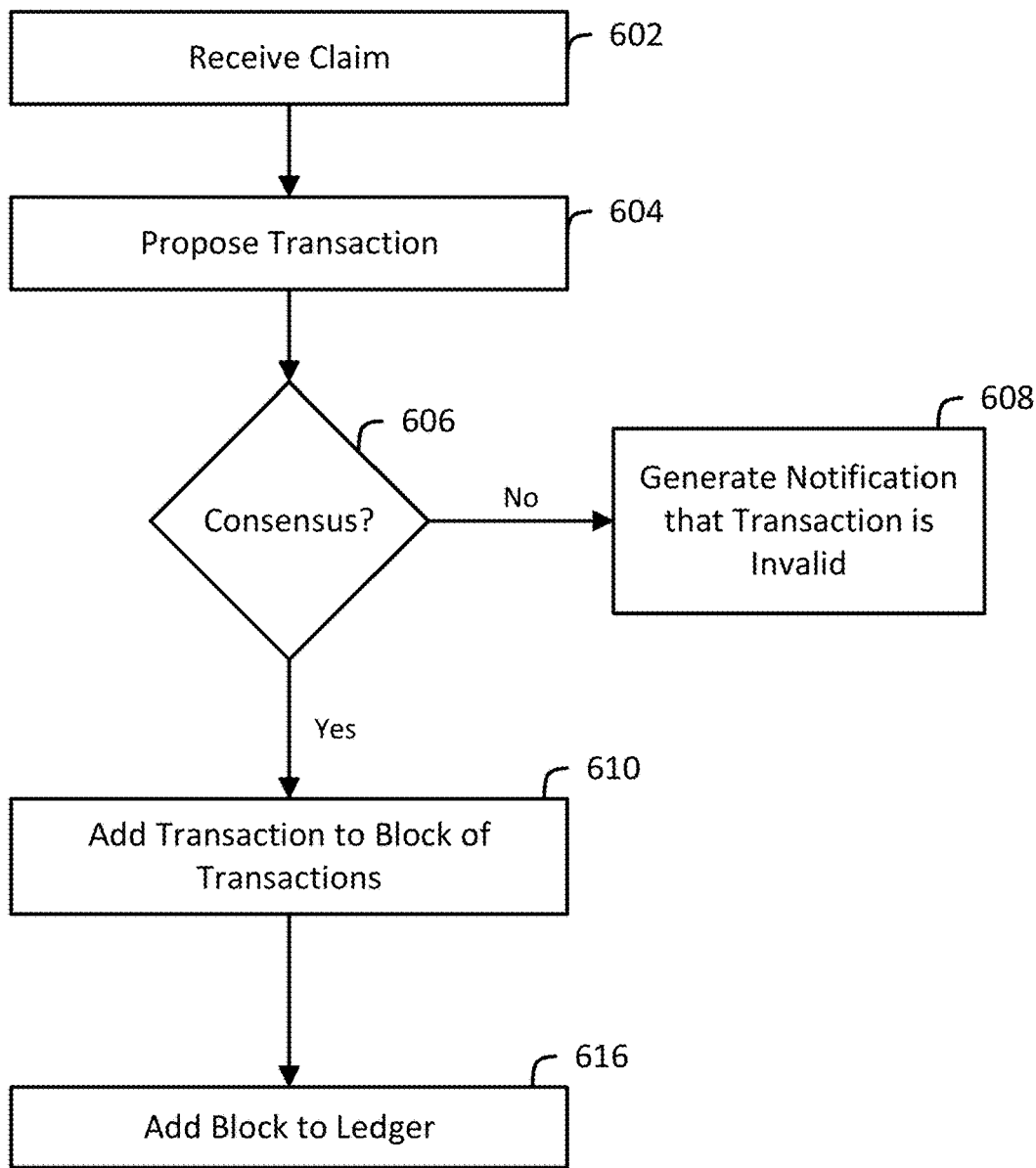
FIG. 6A depicts an example computer-implemented method for tracking a loss history utilizing a distributed ledger in accordance with one aspect of the present disclosure.

FIG. 6A depicts an exemplary computer-implemented method 600 for tracking a loss history utilizing a distributed ledger. The method 600 may be implemented, in whole or in part, by the system 112 shown in FIG. 1B. The method 600 may be saved to a memory as one or more instructions or routines.

The method 600 begins when someone files a claim with Alpha (block 602). After Alpha receives the claim, the node 102 generates a transaction including information pertaining to the claim and proposes the transaction by transmitting the transaction to nodes 104 and/or 106 (block 604). The nodes 102, 104, and 106 then attempt to form a consensus, using any suitable consensus protocol (such as the hashing and problem solving technique previously described) as to whether the transaction is valid (block 606). In instances when consensus is not reached, the proposed transaction is not added to the ledger 114$m$ and notification that the transaction is invalid may be generated (block 608).

When consensus is reached, each of the nodes 102, 104, and 106 adds the transaction to a block (block 610), and the block, if not already part of the blockchain, is added to the blockchain (block 616) stored at the distributed ledger 114. Advantageously, after the blockchain has been updated, each of the nodes 102, 104, and 106 can access and review the transaction including the information pertaining to the new claim. Indeed, in one embodiment, any party having access and permission to the blockchain at the ledger 114 may easily generate a report by reviewing, via the ledger 114, all claims associated with a particular property. Consequently, the method 600 eliminates the need for a third party intermediary that aggregates claim histories from multiple insurance company.

Figure 6B:
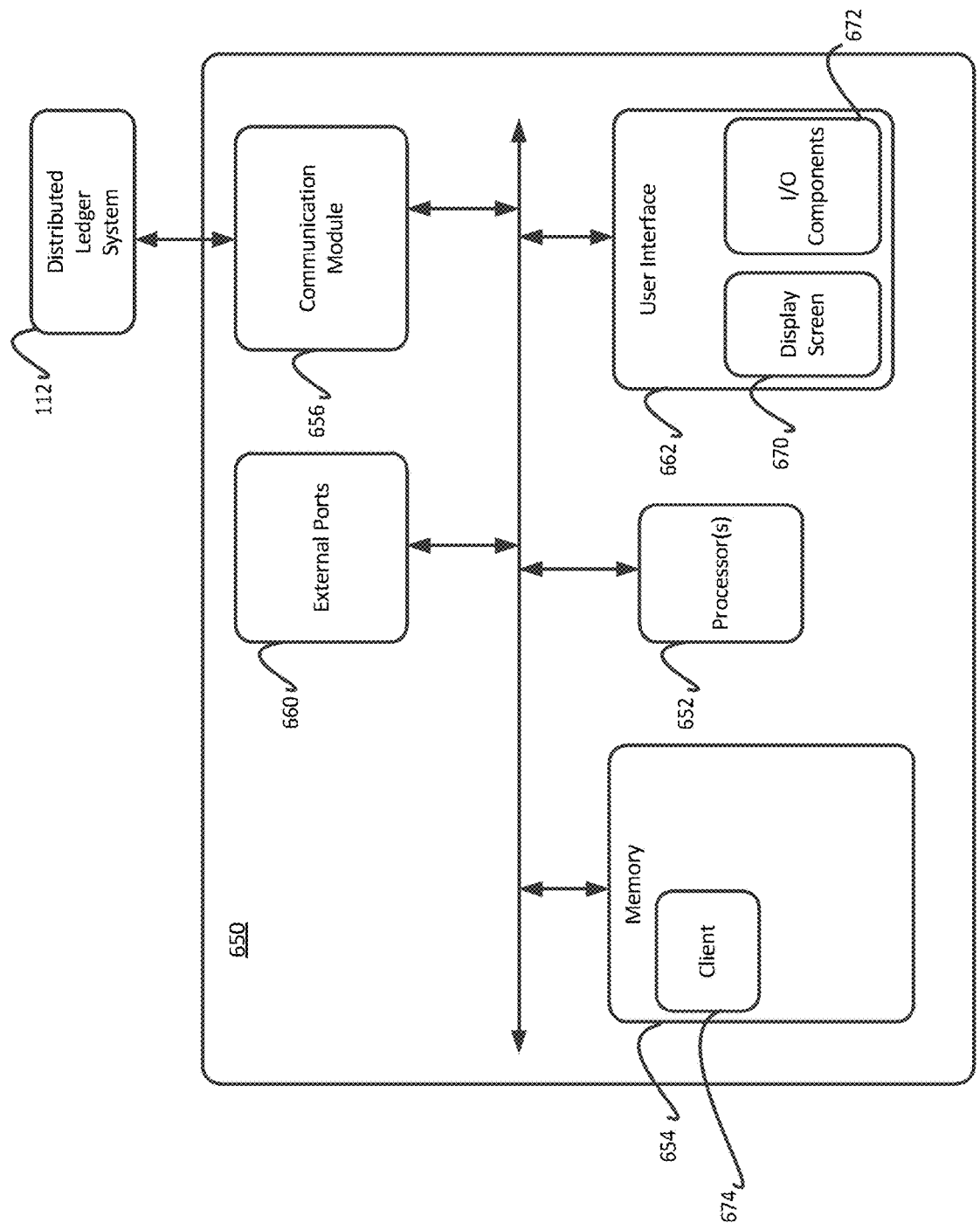
FIG. 6B is a block diagram of a client device that may interact with a distributed ledger system in accordance with one aspect of the present disclosure.

FIG. 6B is a block diagram of a client device 650 that may interact with the system 112 in one embodiment. The client device 650 may include a processor 652 and one or more of the following, which may be connected to the processor 652 via a system bus: a memory 654 including a client application 674, a communication module 656, external ports 660, and a user interface 662. The user interface 662 may include a display screen 670 and/or other I/O components 672. The communication module 656 may be communicatively coupled to the distributed ledger system 112 shown in FIG. 1B, enabling the client device 650 to communicate with one or more of the nodes 102-106 and to access to the distributed ledger 114.

In example operation, the processor 652 executes the client 674, causing the client device 650 to communicate with the system 112 via the communication module 656. The client device 650 may transmit a request for a loss history report pertaining to a particular individual. The client device 650 may transmit a unique identifier for the individual. In response, one of the nodes 102-106 responds by transmitting a report including the pertinent transaction records for all insurance claims for the individual of interest after performing a lookup on a local copy of the distributed ledger 114.

In one embodiment, the client device 650 is part of the system 112. For example, the memory 654 may include a copy of the distributed ledger 114 and/or the blockchain manager 414. In such instances, the client device 50 is a node of the system 112, and thus may be considered a server hosting a copy of the ledger 114. In such an embodiment, when a user of the client device 650 requests a loss history report via the user interface 662, the processor 652 retrieves the pertinent transaction records for all insurance claims for the individual of interest from a copy of the distributed ledger 114 stored at the memory 654.

FIG. 6C is an example loss history report 680 that may be generated by one of the nodes 102-106 and/or client device 650 in one embodiment. The lost history report 680 may be displayed on a display device such as the screen 670 and/or may be printed. The loss history report 680 may be generated in response to a request submitted by a user via the user interface 662 of the client device 650 and transmitted to the distributed ledger system 112 via the communication module 656.

The loss history report 680 may include: a date of order 681 indicating a date on which the report 680 was ordered; a date of receipt 682 indicating a date on which the report 680 was received; a reference number 683 unique to the report 680 (this may be useful if multiple reports are pulled on a single property); a recap 684 identifying a number of claims reported on the property or person searched; and a search summary 685. The search summary 685 may identify a person and/or property being searched; a person who owns the property being searched; a date of birth for the person; a unique identifier, such as a social security number, for the person, a sex of the person; and/or a telephone number for the person. The property may be a real estate property, such as a home or office building. In some embodiments, the property is personal property, such as a vehicle, jewelry, electronics, paintings, antiques, and/or other personal belongings or insured assets.

The loss history report 680 may list all recent insurance claims filed by an individual or insured, and/or all recent insurance-related transactions associated with the individual or insured. In other words, the report may be individual-based or individual centric. The loss history report 680 may additionally or alternatively list all recent insurance claims filed associated with an insured asset, such as a vehicle or home, and/or all recent insurance-related transactions associated with the insured asset. In other words, the report may be insurable-asset based or insurable-asset centric.

Sensor-Based Insurance Systems

In one embodiment, a distributed ledger is utilized manage data associated with sensor-based insurance systems. While some vehicle systems collect certain types of sensor data, this sensor data is generally locally available to an in-vehicle computer. In some instances, the sensor data may be uploaded to a centralized server (e.g., maintained by an insurance company for the purpose of monitoring driving habits).

Figure 7:
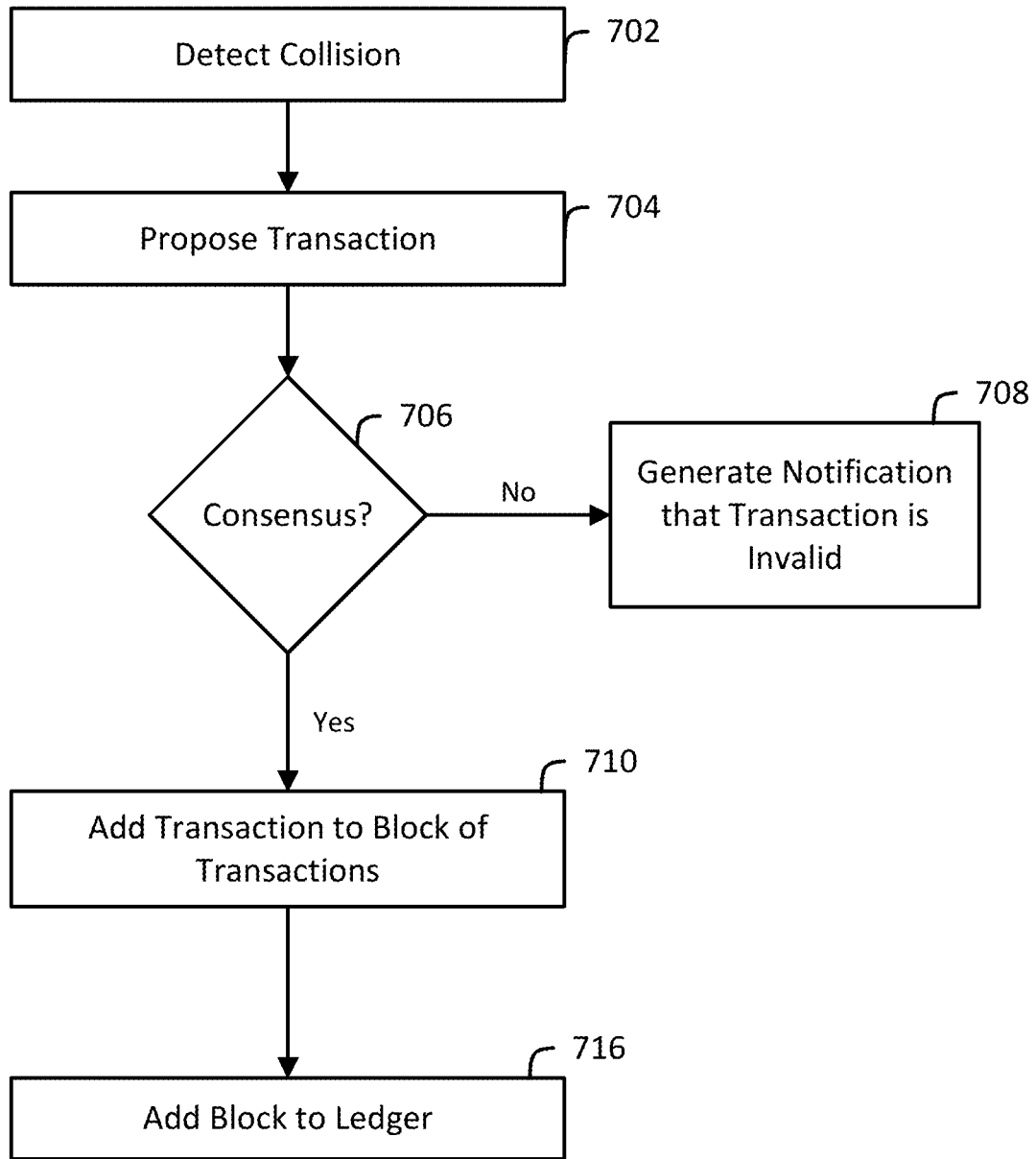
FIG. 7 depicts, in accordance with one aspect of the present disclosure, an exemplary computer-implemented method for tracking, via a distributed ledger, sensor data and other information related to a claim, such as: an estimated damage, an estimated cost of repairs, and/or a payment status for a rental vehicle.

FIG. 7 depicts an exemplary computer-implemented method 700 for tracking, via a distributed ledger, sensor data and other information related to a claim, such as: an estimated damage, an estimated cost of repairs, and/or a payment status for a rental vehicle. The method 700 may be implemented, in whole or in part, by the system 112 shown in FIG. 1B. The method 700 may be saved to a memory as one or more instructions or routines.

The method 700 begins when a collision is detected (block 702). The collision may be detected from various types of sensor and vehicle data, such as data collected via any of a number of suitable sensors at a vehicle, including accelerometers, speedometers, GPS sensors, impact sensors, etc. The sensor and vehicle data may include telematics data (which may include speed, GPS, heading, route, cornering, braking, acceleration, deceleration, and other types of information). The sensor and vehicle data may include mobile device sensor data, which may include some types of telematics data. The sensor and vehicle data may include image, radar, telematics, and other data collected by one or more smart or autonomous vehicles, such as there may several vehicles in the vicinity of a vehicle collision at the time of collision, and sensor data from the several vehicles may be collected, and analyzed.

After detecting the collision, the node 102 (which may be a computer installed in the vehicle or a mobile device such as a tablet or smart phone, depending on the embodiment) generates a transaction including sensor data pertaining to the collision. In a manner similar to that described with reference to blocks 604-616, the transaction is proposed, the nodes attempt to reach consensus, and the transaction is added to the ledger 114 when consensus is reached (blocks 704-716).

Advantageously, after the ledger 114 has been updated, each of the nodes 102, 104, and 106 can access and review the transaction including the sensor data and associated information pertaining to a claim. One or more systems may access the ledger 114 to estimate damage and/or cost of repairs based upon the sensor data, and may similarly update the ledger 114 to include this information. Notably, the method 700 gives a user access to data relating to his or her collision; he or she may not have to interact with a gatekeeper responsible for maintaining information at a centralized database.

In another example, one or more home-based "smart devices," claim assessment drones, and/or an insurance company may utilize the ledger 114 to track information related to a real estate claim, such as: estimated damage to a home, estimated repair costs, payouts associated with the claim, third parties to be receive payouts, etc.

In yet another example, one or more vehicles and an insurance company may utilize the ledger 114 to track sensor data for the purpose of updating a UBI profile, such as a profile used to estimate Usage-Based Insurance (e.g., pay-by-mile). Such an example similarly offers a user the advantage of having access to his or her data that might otherwise be stored at a centralized database.

Medical Record Systems

In one embodiment, a distributed ledger is utilized manage medical record systems. Currently, medical records are often held by a multitude of different institutions, each of which maintains its own centralized database including an incomplete record of a patient's medical history (e.g., relating to only a certain period of time or to certain specialty procedures). By contrast, the disclosed system enables aggregation of a complete medical history (to the extent desired), and gives a patient access to records of his or her medical records. In particular, the disclosed system may be utilized to track medical records associated with particular insurance claims.

Figure 8:
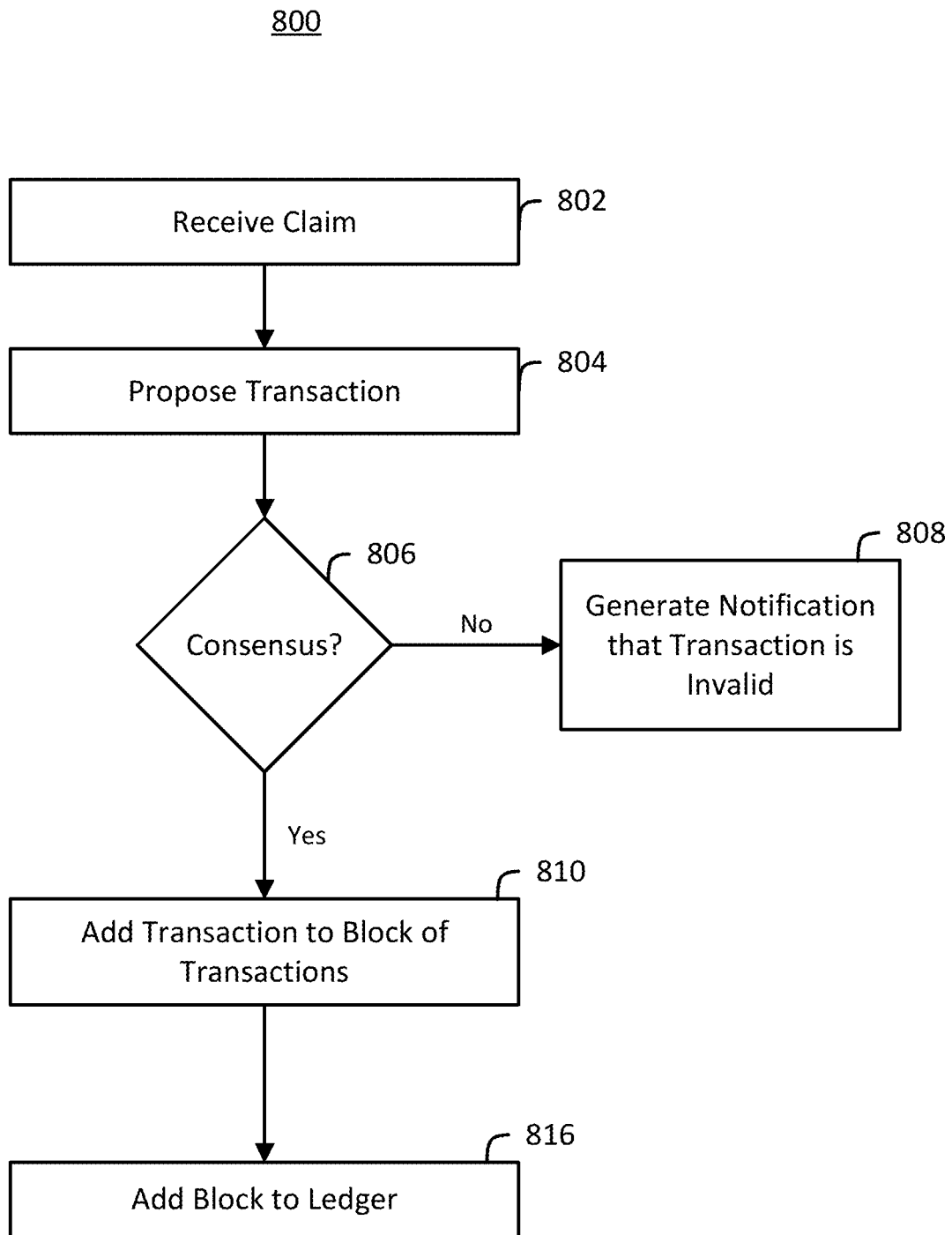
FIG. 8 depicts, in accordance with one aspect of the present disclosure, an exemplary computer-implemented method for managing, via a distributed ledger, medical records related to a claim, such as: an injury description; one or more medical costs; one or more payout amounts; etc.

FIG. 8 depicts an exemplary computer-implemented method 800 for managing, via a distributed ledger, medical records related to a claim, such as: an injury description; one or more medical costs; one or more payout amounts; etc. The method 800 may be implemented, in whole or in part, by the system 112 shown in FIG. 1B. The method 800 may be saved to a memory as one or more instructions or routines.

The method 800 begins when a claim is filed (e.g., after a vehicle collision) (block 802). After the claim is received, the node 102 generates a transaction including data pertaining to the claim, and more particularly, to medical records associated with an injury resulting from the event that led to the claim. In a manner similar to that described with reference to blocks 604-616, the transaction is proposed, the nodes attempt to reach consensus, and the transaction is added to the ledger 114 when consensus is reached (blocks 804-816).

One or more systems may access the ledger 114 to facilitate processing a claim associated with the transaction. Further, the method 800 gives a patient and/or an insurance company (when permitted) access to his or her medical records, which typically is maintained at a centralized database at a health care institution or at a service provider associated with the health care institution.

Insurance Record Management Systems

In one embodiment, a distributed ledger may be utilized to manage insurance record management systems. Currently, insurance records are generally held by individual insurance companies and are not readily available to third parties who wish, for example, to verify that a person is currently insured. By contrast, the disclosed system may manage insurance records via a distributed ledger, enabling multiple parties to easily verify a person's insurance policy.

Figure 9:
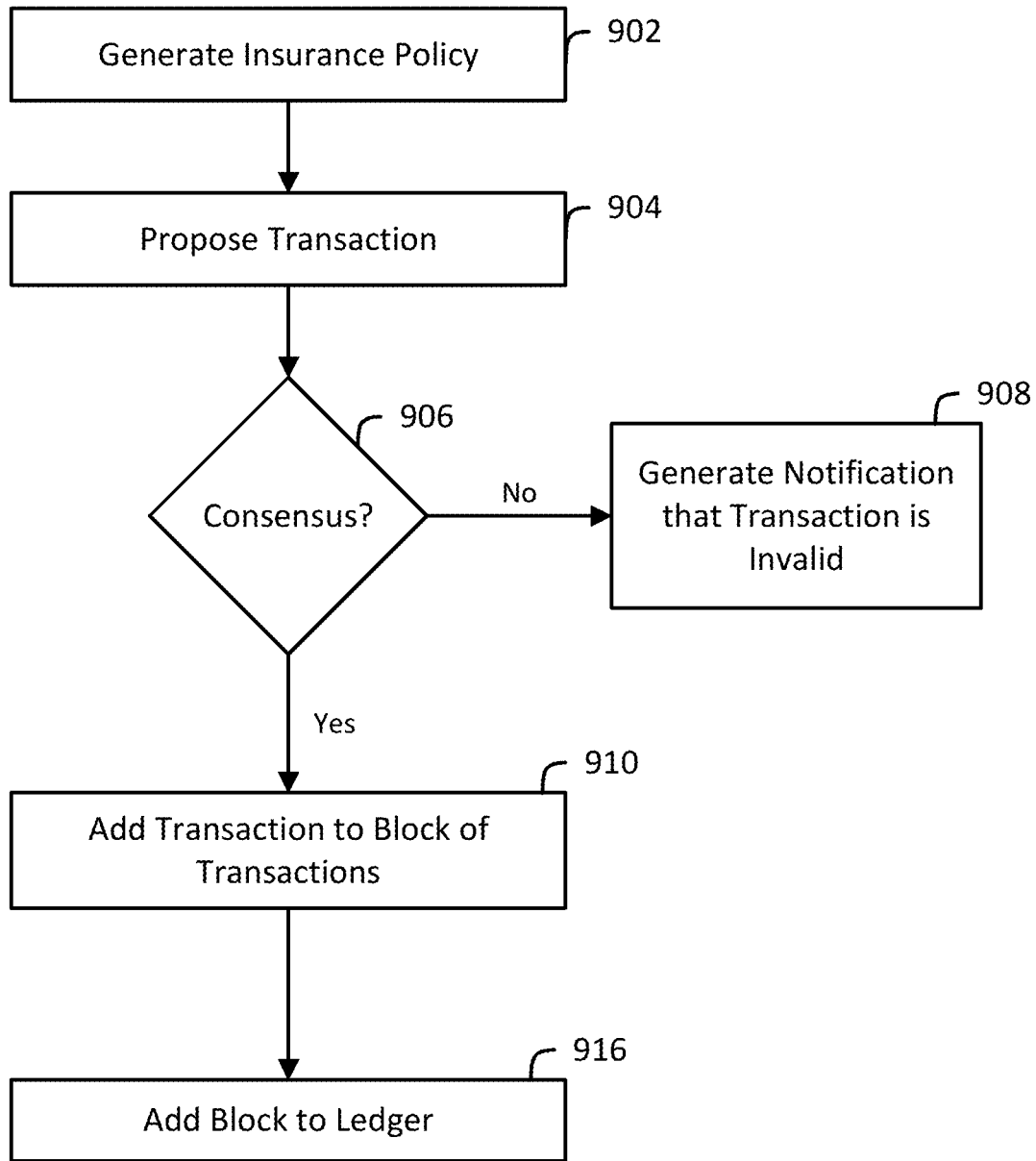
FIG. 9 depicts, in accordance with one aspect of the present disclosure, an exemplary computer-implemented method for managing, via a distributed ledger, insurance records, such as: a unique identifier for the insured; one or more policy numbers associated with the insured; descriptions of each policy for each policy number; coverage amounts; etc.

FIG. 9 depicts an example method 900 for managing, via a distributed ledger, insurance records, such as: a unique identifier for the insured; one or more policy numbers associated with the insured; descriptions of each policy for each policy number; coverage amounts; etc. The method 900 may be implemented, in whole or in part, by the system 112 shown in FIG. 1B. The method 900 may be saved to a memory as one or more instructions or routines.

The method 900 begins when an insurance policy is generated for someone (block 902). The generated policy could be for any suitable insurance product, such as home insurance, vehicle insurance, umbrella insurance, life insurance, etc. After the policy is generated, the node 102 generates a transaction including data pertaining to the policy. In a manner similar to that described with reference to blocks 604-616, the transaction is proposed, the nodes attempt to reach consensus, and the transaction is added to the ledger 114 when consensus is reached (blocks 904-916).

One or more systems may access the ledger 114 to lookup information pertaining to someone's insurance. For example, when a driver is pulled over by law enforcement for speeding, he or she may wish to verify his insurance policy by granting a law enforcement official permission to view his or her insurance records stored on the ledger 114. Advantageously, the method 900 could consequently eliminate the need to carry physical proof of insurance. Further, the method 900 could be utilized to make the exchange of insurance information after an accident more efficient.

Additional Exemplary Loss History

In the insurance industry, loss history may have several meanings. Loss history may include or comprise a report detailing information or data from multiple insurers about an individual's insurance claim history and other asset/insured related information. For instance, loss history may detail the insurance claims filed or reported by an insured, or insurance claims filed relating to an insured asset, such as an automobile or home.

Insurance provider remote servers may report their data to a private or public blockchain, and then the blockchain may generate a consumer's history report independently of 3rd party data aggregators. For instance, the blockchain may include up-to-date information about an insured vehicle, an insured home, other insured assets, and/or about individual customers. The information maintained on the block may include insurance claim information, including amount of claim, and various types of sensor information (telematics, smart vehicle, mobile device, smart home, smart infrastructure, and other sensor data).

Insurance provider remote servers may submit information to the blockchain on real-time or periodic basis. In one embodiment, insurance companies may request data by forwarding search criteria such as an insurance applicant's name, date of birth, risk address, social security numbers (SSNs), etc. An electronic search tool or engine may search a shared ledger for information that matches the requested search criteria and delivers results of the search.

In one aspect, the blockchain may act as an event registry that updates information on the blockchain each time there is an event. For instance, a vehicle-based blockchain may update information each time there is new information, or a change in information, related to the vehicle owner, the insured, or the vehicle, including change of addresses, new insurance claims, vehicle maintenance/repair events, etc. As another example, a home-based blockchain update information on the chain each time there is new information, or a change in information, related to the home or the homeowner (or the insured), including payment of taxes and/or insurance, and/or new insurance claims and home repairs/maintenance.

Exemplary Methods of Maintaining a Blockchain

Figure 10:
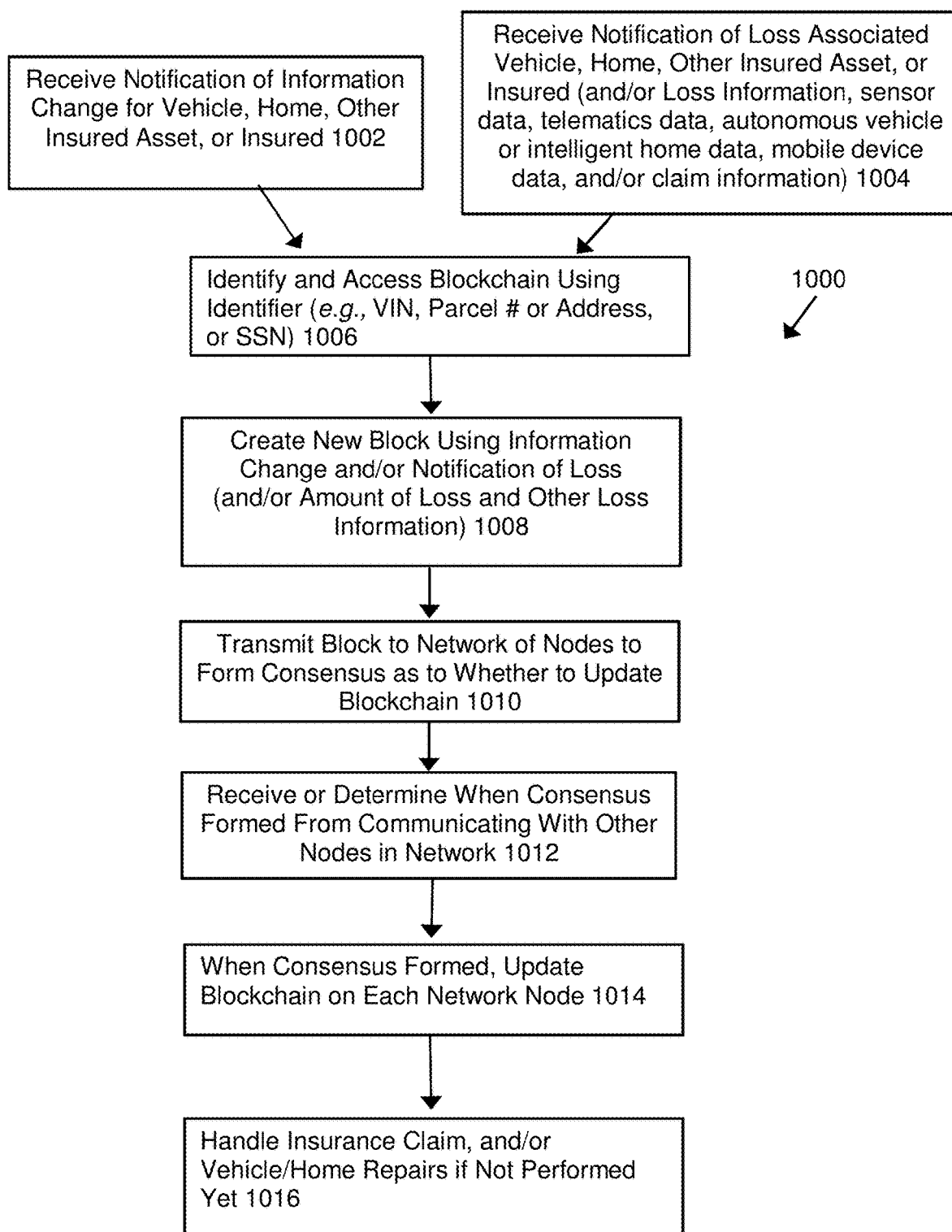
FIGS. 10-13 depict exemplary computer-implemented methods of maintaining a blockchain associated with insured assets and/or individuals.

FIG. 10 depicts an exemplary computer-implemented method of maintaining a blockchain on insured assets or individuals 1000. The method 1000 may include, via one or more local or remote processors, sensors, servers, and/or transceivers, (1) receiving a notification of, or associated with, a change in information associated with an insured and/or an insured vehicle, insured home, insured personal articles, and/or other insured assets 1002; and/or (2) receiving a notification of, or associated with, a loss associated with an insured, or an insured vehicle, insured home, insured personal articles, and/or other insured assets 1004. The notification of loss may include loss information, claim information, various sensor data, telematics data, autonomous vehicle sensor or other data, intelligent home sensor or other data, mobile device data, and/or other data about insureds and insured assets, including that discussed elsewhere herein). For instance, the notifications may be received via wireless communication or data transmission over one or more radio frequency links or digital communication channels, and stored in a local memory.

The method 1000 may include, via one or more local or remote processors, sensors, servers, and/or transceivers, (3) identifying and/or accessing a blockchain using an identifier associated with both the blockchain and an insured and/or insured asset 1006. For instance, a VIN (Vehicle Identification Number) may be used to identify and/or access an insured vehicle and an associated blockchain. A SSN may be used to identify and/or access an insured and an associated blockchain. An address, MLS listing, or tax parcel number may be used to identify and/or access an insured home and an associated blockchain. In some embodiments, the identifiers may hashed and/or encrypted, along with other data and/or blocks within the blockchain.

The method 1000 may include, via one or more local or remote processors, sensors, servers, and/or transceivers, (4) creating a new block using the new information (or changed information) and/or the notification of loss information, and/or an amount of loss and other loss information 1008. The method 1000 may include, via one or more local or remote processors, sensors, servers, and/or transceivers, (5) transmitting the new block to a network of nodes to form a consensus among the nodes as whether or not to update the blockchain 1010. For instance, the new block may be transmitted to other nodes within a network via wireless communication or data transmission over one or more radio links.

The method 1000 may include, via one or more local or remote processors, sensors, servers, and/or transceivers, (6) receiving or determining when a consensus is formed from communicating with other nodes in the networks 1012. When a consensus if formed, the method 1000 may include, via one or more local or remote processors, sensors, servers, and/or transceivers, (7) updating the blockchain, on each node, with the new block 1014, and (8) handling or updating an insurance claim for an insured asset, and/or facilitating repairs for an insured asset 1016 if not yet performed or still necessary. The method may include additional, less, or alternate actions, including those discussed elsewhere herein, and/or may be carried out by computer systems comprising of one or more processors, servers, sensors, and/or transceivers configured to perform the functionality and/or via computer-executable instructions stored on computer readable medium or media.

Figure 11:
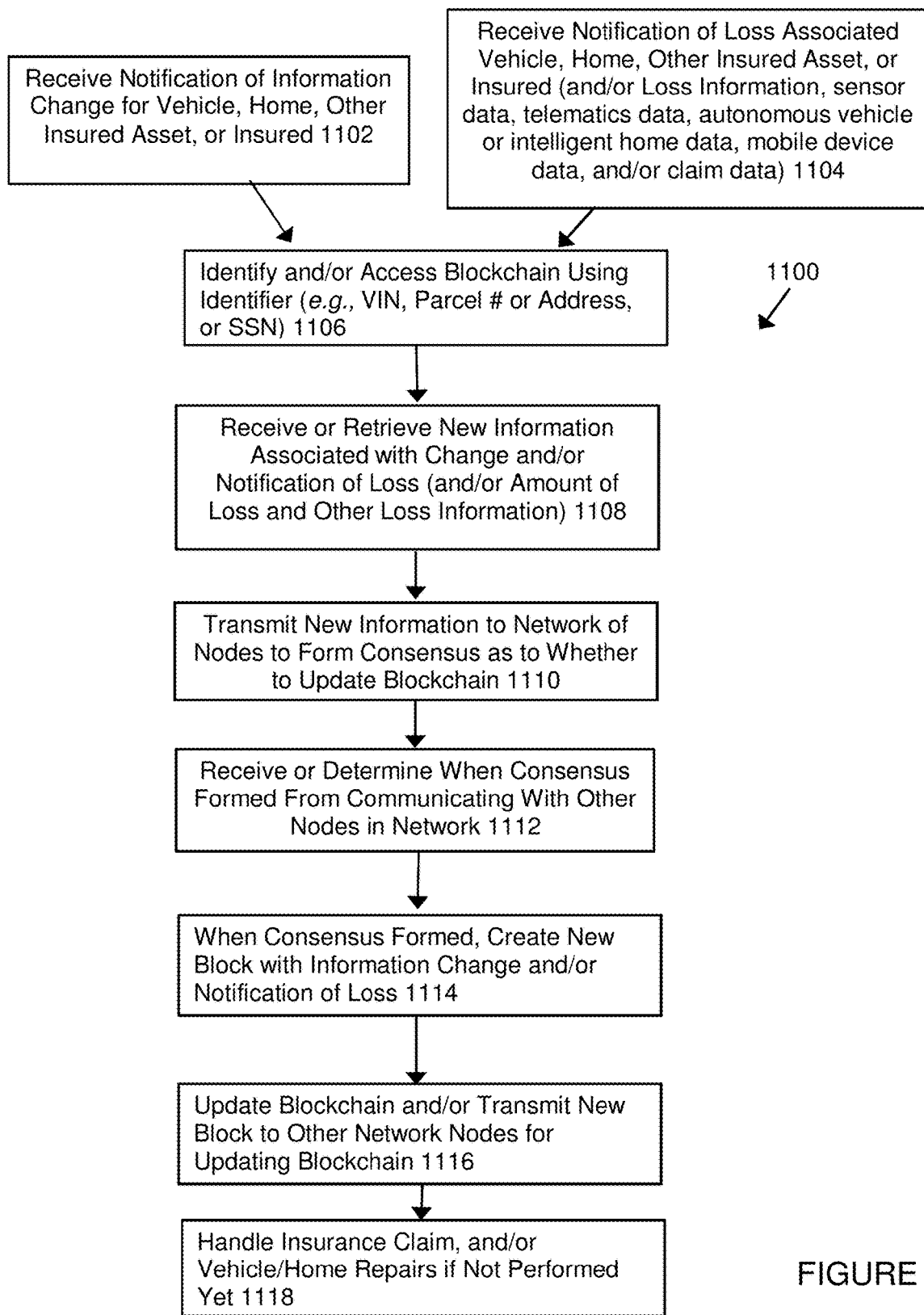

FIG. 11 depicts another exemplary computer-implemented method of maintaining a blockchain associated with insured assets and/or individuals 1100. The method 1100 may include, via one or more local or remote processors, sensors, servers, and/or transceivers, (1) receiving a notification of, or associated with, a change in information associated with an insured and/or an insured vehicle, insured home, insured personal articles, and/or other insured assets 1102; and/or (2) receiving a notification of, or associated with, a loss associated with an insured, or an insured vehicle, insured home, insured personal articles, and/or other insured assets 1104. The notification of loss may include loss information, claim information, various sensor data, telematics data, autonomous vehicle sensor or other data, intelligent home sensor or other data, mobile device data, and/or other data about insureds and insured assets, including that discussed elsewhere herein). For instance, the notifications may be received via wireless communication or data transmission over one or more radio frequency links or digital communication channels, and stored in a local memory.

The method 1100 may include, via one or more local or remote processors, sensors, servers, and/or transceivers, (3) identifying and/or accessing a blockchain using an identifier associated with both the blockchain and an insured and/or insured asset 1106. For instance, a VIN (Vehicle Identification Number) may be used to identify and/or access an insured vehicle and an associated blockchain. A SSN may be used to identify and/or access an insured and an associated blockchain. An address, MLS listing, or tax parcel number may be used to identify and/or access an insured home and an associated blockchain. In some embodiments, the identifiers may hashed and/or encrypted, along with other data and/or blocks within the blockchain.

The method 1100 may include, via one or more local or remote processors, sensors, servers, and/or transceivers, (4) receiving or retrieving from a memory new information associated with a change in information and/or a notification of loss (and/or amount and type of loss) 1408. The method 1100 may include, via one or more local or remote processors, sensors, servers, and/or transceivers, (5) transmitting the new information to a network of nodes to form a consensus among the nodes as whether or not to update the blockchain 1110. For instance, the new block may be transmitted to other nodes within a network via wireless communication or data transmission over one or more radio links.

The method 1100 may include, via one or more local or remote processors, sensors, servers, and/or transceivers, (6) receiving or determining when a consensus is formed from communicating with other nodes in the networks 1112. When a consensus if formed, the method 1100 may include, via one or more local or remote processors, sensors, servers, and/or transceivers, (7) creating a new block using the new information (or changed information) and/or the notification of loss information, and/or an amount of loss and other loss information 1114, and (8) updating the blockchain, on each node, with the new block 1116, or otherwise updating the blockchain on each node with the new information. The method 1100 may also include, via one or more local or remote processors, sensors, servers, and/or transceivers, (9) handling or updating an insurance claim for an insured asset, and/or facilitating repairs for an insured asset 1118 if not yet performed or still necessary. The method may include additional, less, or alternate actions, including that discussed elsewhere herein, and/or may be carried out by computer systems comprising of one or more processors, servers, sensors, and/or transceivers configured to perform the functionality and/or via computer-executable instructions stored on computer readable medium or media.

Figure 12:
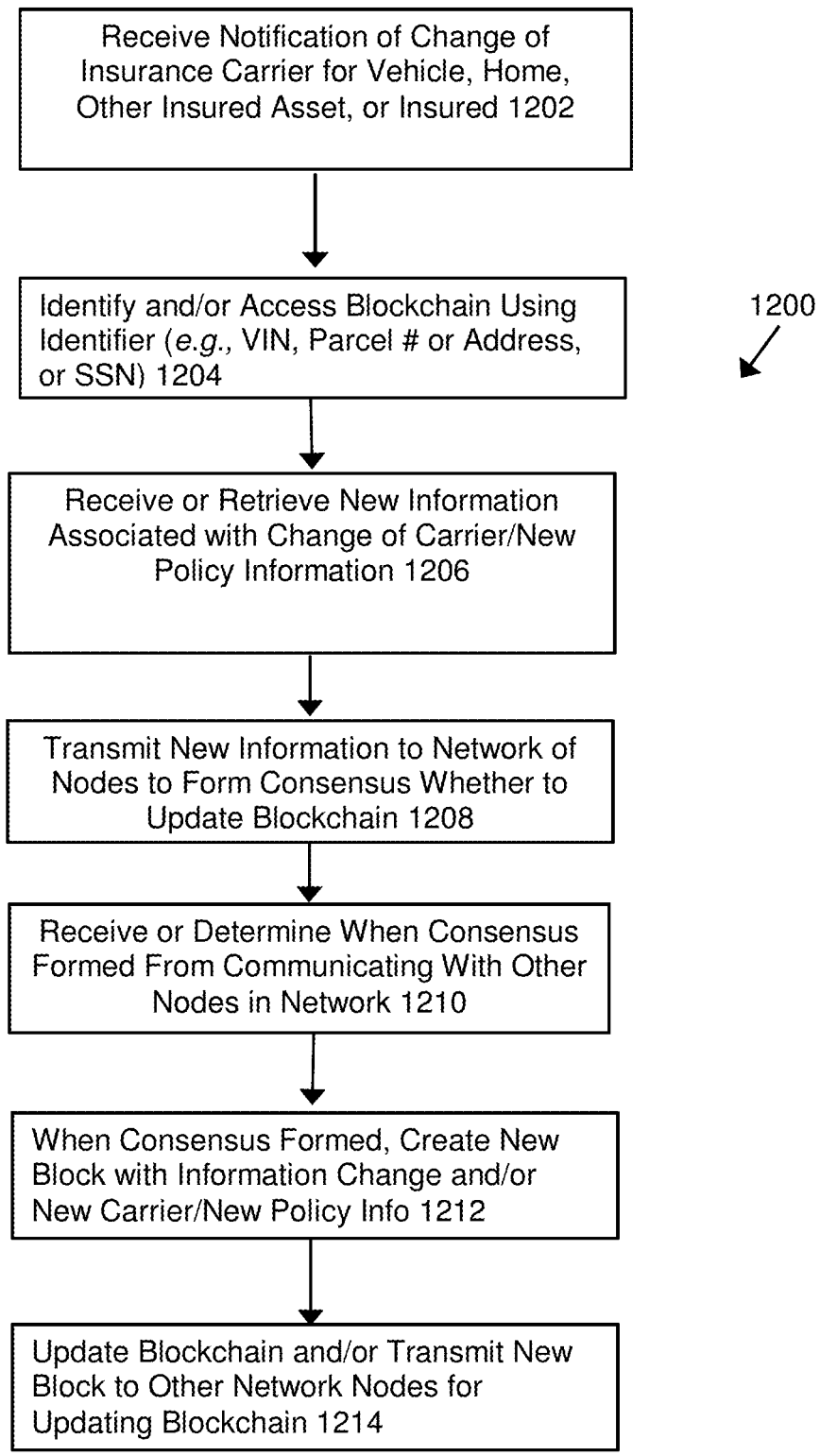

FIG. 12 depicts another exemplary computer-implemented method of maintaining a blockchain associated with insured assets and/or individuals 1200. The method 1200 may include, via one or more local or remote processors, sensors, servers, and/or transceivers, (1) receiving a notification of, or associated with, a change in information associated with an insured and/or an insured vehicle, insured home, insured personal articles, and/or other insured assets 1202, such as from a node associated with an insurance provider or from an insurance provider remote server. For instance, the notifications may be received via wireless communication or data transmission over one or more radio frequency links or digital communication channels, and stored in a local memory.

The method 1200 may include, via one or more local or remote processors, sensors, servers, and/or transceivers, (2) identifying and/or accessing a blockchain using an identifier associated with both the blockchain and an insured and/or insured asset 1204. For instance, a VIN (Vehicle Identification Number) may be used to identify and/or access an insured vehicle and an associated blockchain. A SSN may be used to identify and/or access an insured and an associated blockchain. An address, MLS listing, or tax parcel number may be used to identify and/or access an insured home and an associated blockchain. In some embodiments, the identifiers may hashed and/or encrypted, along with other data and/or blocks within the blockchain.

The method 1200 may include, via one or more local or remote processors, sensors, servers, and/or transceivers, (3) receiving or retrieving from a memory new information associated with a change in information and/or a change in carrier (or otherwise a new carrier) 1506. The method 1200 may include, via one or more local or remote processors, sensors, servers, and/or transceivers, (4) transmitting the new information (such as identification of a new carrier and/or new policy information) to a network of nodes to form a consensus among the nodes as whether or not to update the blockchain 1208. For instance, the new block may be transmitted to other nodes within a network via wireless communication or data transmission over one or more radio links.

The method 1200 may include, via one or more local or remote processors, sensors, servers, and/or transceivers, (5) receiving or determining when a consensus is formed from communicating with other nodes in the networks 1210. When a consensus if formed, the method 1200 may include, via one or more local or remote processors, sensors, servers, and/or transceivers, (6) creating a new block using the new information (or changed information) and/or the new insurance carrier and/or new insurance policy information 1212, and/or (7) updating the blockchain, on each node, with the new block 1214, or otherwise updating the blockchain on each node with the new information. The method 1200 may also include handling or updating an insurance claim for an insured asset, and/or facilitating repairs for an insured asset if not yet performed or still necessary. The method may include additional, less, or alternate actions, including that discussed elsewhere herein, and/or may be carried out by computer systems comprising of one or more processors, servers, sensors, and/or transceivers configured to perform the functionality and/or via computer-executable instructions stored on computer readable medium or media.

Figure 13:
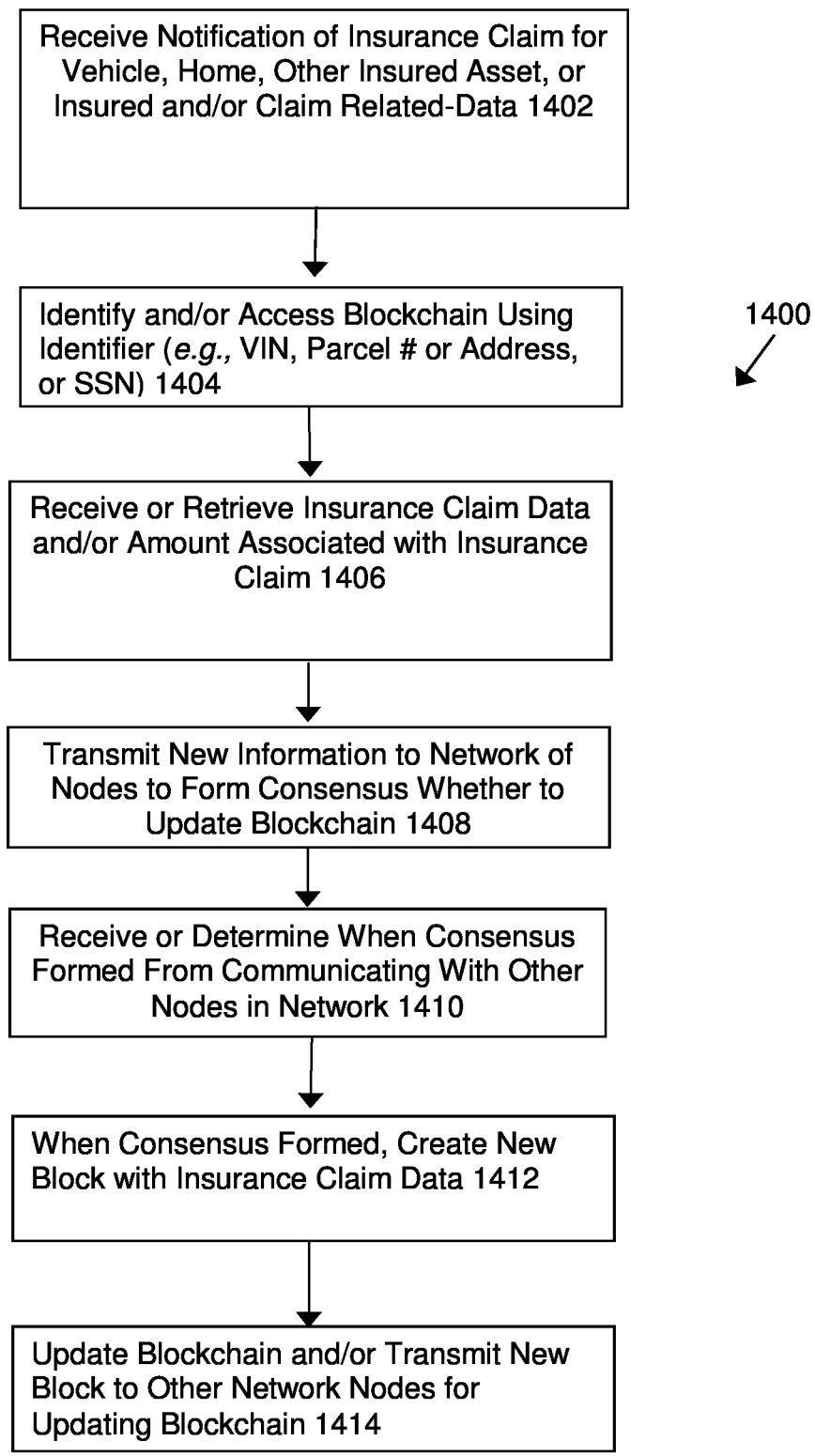
Figure 14:
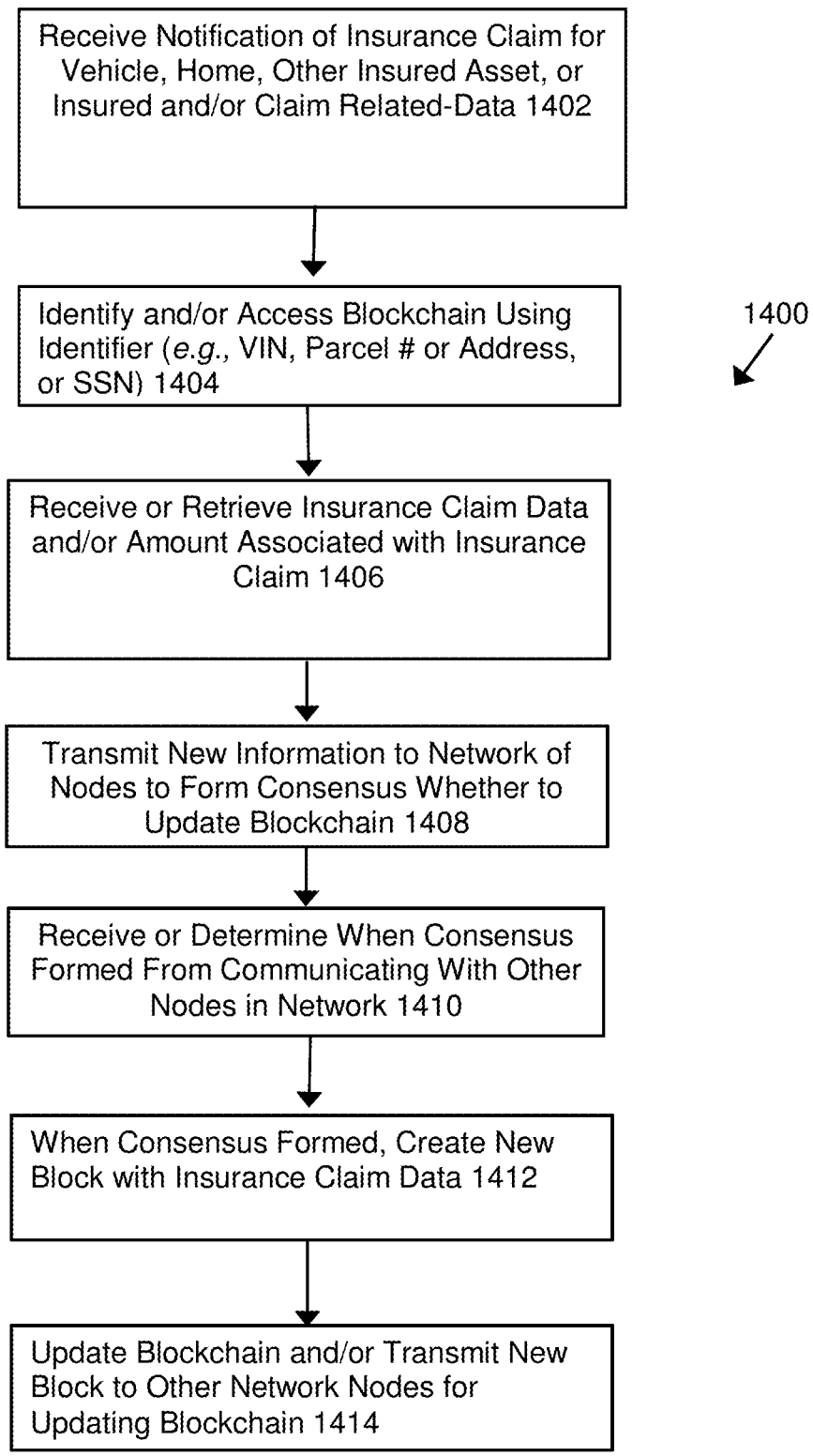

FIG. 13 depicts another exemplary computer-implemented method of maintaining a blockchain on insured assets or individuals 1400. The method 1400 may include, via one or more local or remote processors, sensors, servers, and/or transceivers, (1) receiving a notification of, or associated with, an insurance claim associated with an insured and/or an insured vehicle, insured home, insured personal articles, and/or other insured assets, and/or receiving insurance claim related data 1402, such as from a node associated with an insurance provider or from an insurance provider remote server. For instance, the notifications may be received via wireless communication or data transmission over one or more radio frequency links or digital communication channels, and stored in a local memory.

The method 1400 may include, via one or more local or remote processors, sensors, servers, and/or transceivers, (2) identifying and/or accessing a blockchain using an identifier associated with both the blockchain and an insured and/or insured asset 1404. For instance, a VIN (Vehicle Identification Number) may be used to identify and/or access an insured vehicle and an associated blockchain. A SSN may be used to identify and/or access an insured and an associated blockchain. An address, MLS listing, or tax parcel number may be used to identify and/or access an insured home and an associated blockchain. In some embodiments, the identifiers may hashed and/or encrypted, along with other data and/or blocks within the blockchain.

The method 1400 may include, via one or more local or remote processors, sensors, servers, and/or transceivers, (3) receiving or retrieving from a memory new information associated with an insurance claim and/or an amount associated with an insurance claim 1406. The method 1400 may include, via one or more local or remote processors, sensors, servers, and/or transceivers, (4) transmitting the new information (such as identification of a new insurance claim and policy information) to a network of nodes to form a consensus among the nodes as whether or not to update the blockchain 1408. For instance, the new block may be transmitted to other nodes within a network via wireless communication or data transmission over one or more radio links.

The method 1400 may include, via one or more local or remote processors, sensors, servers, and/or transceivers, (5) receiving or determining when a consensus is formed from communicating with other nodes in the networks 1410. When a consensus if formed, the method 1400 may include, via one or more local or remote processors, sensors, servers, and/or transceivers, (6) creating a new block using the new insurance claim data and/or policy data 1412, and/or (7) updating the blockchain, on each node, with the new block 1414, or otherwise updating the blockchain on each node with the new insurance claim information. The method 1400 may also include handling or updating an insurance claim for an insured asset, and/or facilitating repairs for an insured asset if not yet performed or still necessary. The method may include additional, less, or alternate actions, including that discussed elsewhere herein, and/or may be carried out by computer systems comprising of one or more processors, servers, sensors, and/or transceivers configured to perform the functionality and/or via computer-executable instructions stored on computer readable medium or media.

In one exemplary flow, a computer-implemented method may include (1) receiving, at a processor coupled with a network interface (such as via wireless communication or data transmission over one or more radio links), an insurance claim notification from at least a first participant, wherein the claim notification comprises an insured asset identifier, and an insured asset owner identifier; (2) retrieving or accessing, at a memory coupled with a processor, the blockchain using the insured asset identifier and/or insured asset owner identifier. The method may include (3) updating, at the memory, a block stored at the memory using the insured asset identifier and/or insured asset owner identifier; and (4) transmitting, via the processor coupled with the network interface (such as via wireless communication or data transmission over one or more radio links), the block to at least a second participant or node within a private or public communication network.

In some embodiments, insured asset may be a vehicle, a home, or a personal article. The first participant or node may be a sensor, a sensor system, or computer system attached to the insured asset, such as an autonomous vehicle technology system mounted on a vehicle. In other embodiments, the first participant or node may be a repair shop server or computer system. Similarly, in some embodiments, accessing the blockchain using the insured asset identifier or the insured identified may include searching, at the processor, the blockchain using the insured asset identifier or insured identifier for a block or blockchain that includes the insured asset identifier or insured identifier; and verifying, at the processor, the insured asset identifier or insured identifier stored at the block.

In other embodiments, if the insured asset identifier is not stored at a block, the method may include generating, at the processor, an insured asset record using the insured asset identifier; adding, at the processor, the insured asset identifier and the insured identifier to an insured asset transaction; adding, at the processor, the insured asset transaction to a set of insured asset loss or other transactions; and adding, at the processor, the set of insured asset loss or other transactions to the block.

In other embodiments, the method may include solving, at the processor, a cryptographic puzzle corresponding to the block; and adding, at the processor, the solution to the cryptographic puzzle to the block. Additionally, in some embodiments, updating, at the memory, the blockchain by adding the block to the blockchain.

In yet other embodiments of the method, the at least one other participant is an insurer, a vehicle owner, a repair shop, or combinations thereof. In some embodiments, the method may include receiving, at the processor, a repair notification from one or more remote servers associated with other parties, such as repair shops or part suppliers.

The blockchains discussed herein may be updated after one or more triggering events are detected. For instance, the triggering events may include change of ownership, passage of time (e.g., every week, month, 3 months, or 6 months), amount of miles put on a vehicle (e.g., 5,000 or 10,000 miles), an amount of time the vehicle has driven, or operated if autonomous, vehicle or home maintenance being performed or not being performed, change of address, change in tax or insurance status, change in lender, change in insurance carrier, etc.

Additional Considerations

With the foregoing, an insurance customer may opt-in to a rewards, insurance discount, or other type of program (such as the UBI program described with reference to FIG. 7). After the insurance customer provides their affirmative consent, an insurance provider remote server may collect data from the customer's mobile device, smart or autonomous vehicle, smart home controller, or other smart devices. The data collected may be related to smart home functionality (or home occupant preferences or preference profiles), smart or autonomous vehicle functionality, and/or insured assets before (and/or after) an insurance-related event, including those events discussed elsewhere herein. In return, risk averse insureds, home or vehicle owners, or home, vehicle, or apartment occupants may receive discounts or insurance cost savings related to home, renters, personal articles, auto, health, life, and other types of insurance from the insurance provider.

In one aspect, telematics data, smart or autonomous vehicle data, mobile device data, smart or interconnected home data, and/or other data, including the types of data discussed elsewhere herein, may be collected or received by an insurance provider remote server (e.g., via direct or indirect wireless communication or data transmission from a smart home controller, mobile device, or other customer computing device) after a customer affirmatively consents or otherwise opts-in to an insurance discount, reward, or other program. The insurance provider may then analyze the data received with the customer's permission to provide benefits to the customer. As a result, risk averse customers may receive insurance discounts or other insurance cost savings based upon data that reflects low risk behavior and/or technology that mitigates or prevents risk to (i) insured assets, such as homes, personal belongings, or vehicles, and/or (ii) individuals.

This detailed description is to be construed as exemplary only and does not describe every possible embodiment, as describing every possible embodiment would be impractical, if not impossible. One may be implement numerous alternate embodiments, using either current technology or technology developed after the filing date of this application.

Further to this point, although the embodiments described herein often utilize credit report information as an example of sensitive information, the embodiments described herein are not limited to such examples. Instead, the embodiments described herein may be implemented in any suitable environment in which it is desirable to identify and control specific type of information. As part of implementing the automotive claims process, vehicle loss history, and the lifecycle of a Vehicle Identification Number, a financial institution may be a part of the process. For example, the aforementioned embodiments may be implemented by the financial institution to identify and contain bank account statements, brokerage account statements, tax documents, etc. To provide another example, the aforementioned embodiments may be implemented by a lender to not only identify, re-route, and quarantine credit report information, but to apply similar techniques to prevent the dissemination of loan application documents that are preferably delivered to a client for signature in accordance with a more secure means (e.g., via a secure login to a web server) than via email.

With the foregoing, a user may be an insurance customer who may opt-in to a rewards, insurance discount, or other type of program. After the insurance customer provides their affirmative consent, an insurance provider remote server may collect data from the customer's mobile device, smart home controller, smart or autonomous vehicle, or other smart devices—such as with the customer's permission or affirmative consent. The data collected may be related to smart vehicle or smart home functionality (or home occupant preferences or preference profiles), and/or insured assets before (and/or after) an insurance-related event, including those events discussed elsewhere herein. In return, risk averse insureds, home or vehicle owners, or drivers may receive discounts or insurance cost savings related to home, renters, personal articles, auto, health or life, and other types of insurance from the insurance provider.

Furthermore, although the present disclosure sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims. Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In exemplary embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

The patent claims at the end of this patent application are not intended to be construed under 35 U.S.C. § 112(f) unless traditional means-plus-function language is expressly recited, such as "means for" or "step for" language being explicitly recited in the claim(s).

What is claimed:

1. A computer-implemented method for tracking medical histories, the method comprising:
   implementing a plurality of servers, each of the plurality of servers maintaining a copy of a distributed ledger;
   tracking, at the distributed ledger, (i) a plurality of insurance claims involving a patient and (ii) medical records associated with each of the plurality of insurance claims, including performing the following when an insurance claim involving the patient is filed:
     (i) generating, at a first server from the plurality of servers, a particular transaction record representing the filed insurance claim, wherein the particular transaction record includes data pertaining to the filed insurance claim and data pertaining to a particular set of medical records associated with the filed medical insurance claim;
     (ii) including transmitting the particular transaction record from the first server to the one or more other servers for a consensus analysis of the transaction record;
     (iii) performing, via the plurality of servers, the consensus analysis of the particular transaction record utilizing a consensus mechanism, wherein performing the consensus analysis includes generating a hash value for the transaction record and utilizing the hash value for the transaction record to generate a hash value for a new block, including the transaction record, for the distributed ledger; and
     (iv) when the consensus analysis indicates that the plurality of servers have formed a consensus, storing the new block including the particular transaction record to each copy of the distributed ledger at the plurality of servers;
   when a request for a medical history report for the patient is received, (i) responding to the request by retrieving, from a copy of the distributed ledger maintained by one of the plurality of server, a medical history pertaining to the patient's filed insurance claims, wherein the medical history includes the medical records associated with each of the plurality of insurance claims and (ii) generating the medical history report based on the retrieved medical history.

2. The method of claim 1, wherein the consensus mechanism is: a proof of work mechanism, a proof of stake mechanism, or a proof of activity mechanism.

3. The method of claim 1, wherein the consensus mechanism is: a proof of burn mechanism, a proof of capacity mechanism, or a proof of elapsed time mechanism.

4. The method of claim 1, wherein the transaction record includes data representing each of: an identity of an insured person, a description of an injury, and one or more medical costs.

5. The method of claim 4, wherein the transaction record further includes data representing a payout amount.

6. The method of claim 1, wherein at least one of the servers is a computer possessed by the patient.

7. The method of claim 1, further including receiving from the patient a list of authorized parties, and wherein the medical history report is only generated when a party requesting the medical history report is on the list of authorized parties.

8. The method of claim 7, wherein the distributed ledger tracks the list of authorized parties.

9. A system for tracking medical histories, the system comprising:
   a plurality of servers each maintaining a copy of a distributed ledger for tracking (i) a plurality of insurance claims involving a patient and (ii) medical records associated with each of the plurality of insurance claims, wherein the plurality of servers includes a first server and one or more other servers;
   wherein the first server includes a memory storing instructions that, when executed, cause the first server to:
     (i) generate a transaction record including (a) data representing a filed insurance claim and (b) data representing medical information pertaining to the patient and to the filed insurance claim; and
     (ii) transmit the transaction record to the one or more other servers for a consensus analysis of the transaction record;
   wherein the one or more other servers from the plurality of servers are configured to: (i) perform the consensus analysis of the transaction record utilizing a consensus mechanism, wherein performing the consensus analysis includes generating a hash value for the transaction record and utilizing the hash value for the transaction record to generate a hash value for a new block, including the transaction record, for the distributed ledger; (ii) store the new block including the transaction record at the distributed ledger when the consensus analysis indicates that the plurality of servers have formed a consensus by storing the transaction record to each copy of the distributed ledger at the plurality of servers; and
   wherein each of the plurality of servers is further configured to perform the following functions in response to receiving a request for a medical history report for the patient by: (i) retrieving, from a copy of the distributed ledger, a medical history pertaining to the patient's filed insurance claims, wherein the medical history includes the medical records associated with each of the plurality of insurance claims involving the patient, and (ii) generating the medical history report based on the retrieved medical history.

10. The system of claim 9, wherein the consensus mechanism is: a proof of work mechanism, a proof of stake mechanism, or a proof of activity mechanism.

11. The system of claim 9, wherein the consensus mechanism is: a proof of burn mechanism, a proof of capacity mechanism, or a proof of elapsed time mechanism.

12. The system of claim 9, wherein the transaction record includes data representing each of: an identity of an insured person, a description of an injury, and one or more medical costs.

13. The system of claim 12, wherein the transaction record further includes data representing a payout amount.

14. The system of claim 9, wherein at least one of the servers is a computer possessed by the patient.

15. The system of claim 9, further including receiving from the patient a list of authorized parties, and wherein the medical history report is only generated when a party requesting the medical history report is on the list of authorized parties.

16. The system of claim 15, wherein the distributed ledger tracks the list of authorized parties.

\* \* \* \* \*